(12) United States Patent
Harrington et al.

(10) Patent No.: US 11,013,831 B2
(45) Date of Patent: May 25, 2021

(54) METHODS OF SYNTHESIS FOR A THIOKETAL DIOL

(71) Applicant: WARSAW ORTHOPEDIC, INC., Warsaw, IN (US)

(72) Inventors: Roger E. Harrington, Collierville, TN (US); Jerbrena C. Jacobs, Hernando, MS (US); Robert Doyle, Worcester, MA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 35 days.

(21) Appl. No.: 16/280,706

(22) Filed: Feb. 20, 2019

(65) Prior Publication Data

US 2020/0261626 A1 Aug. 20, 2020

(51) Int. Cl.
| | | |
|---|---|---|
| *C07C 319/20* | (2006.01) | |
| *A61L 27/58* | (2006.01) | |
| *A61L 27/18* | (2006.01) | |
| *C08G 18/38* | (2006.01) | |
| *A61L 27/40* | (2006.01) | |

(52) U.S. Cl.
CPC ............ *A61L 27/58* (2013.01); *A61L 27/18* (2013.01); *A61L 27/40* (2013.01); *C07C 319/20* (2013.01); *C08G 18/3868* (2013.01); *A61L 2300/40* (2013.01)

(58) Field of Classification Search
CPC .................................................. C07C 319/20
See application file for complete search history.

(56) References Cited

U.S. PATENT DOCUMENTS

| | | | |
|---|---|---|---|
| 5,433,958 | A | 7/1995 | Grislain et al. |
| 8,425,893 | B2 | 4/2013 | Knaack et al. |
| 9,266,824 | B2 | 2/2016 | Harrington et al. |
| 9,463,261 | B2 | 10/2016 | Duvall et al. |
| 9,789,223 | B2 | 10/2017 | Knaack et al. |
| 10,046,086 | B2 | 8/2018 | Guelcher et al. |
| 2017/0119924 | A1 | 5/2017 | Guelcher et al. |
| 2018/0280568 | A1* | 10/2018 | Guelcher ............... A61L 27/18 |

OTHER PUBLICATIONS

Zaidl et al. Synthetic Communications 2007, 37, 2835-2845 (Year: 2007).*
Diisobutylaluminium hydride, Wikipedia, version dated Sep. 8, 2018 (Year: 2018).*
Lithium aluminium hydride, Wikipedia, version dated Sep. 7, 2017 (Year: 2017).*
"Red-Al, Sodium bis(2-methoxyethoxy)aluminumhydride" (https://web.archive.org/web/20170907061241/http://www.organic-chennistry.org/chemicals/reductions/sodiumbis(2-methoxyethoxy)aluminumhydride-red-al.shtm), dated Aug. 30, 2017, Organic Chemistry Portal (Year: 2017).*
McEnery, Madison A. P., et al. "Oxidatively Degradable Poly(thioketal urethane)/Ceramic Composite Bone Cements with Bone-Like Strength" RSC Adv 2016; 6(111): 109414-109424.
Bitar, Khalil N., et al. "Design Strategies of Biodegradable Scaffolds for Tissue Regeneration" Biomed Eng Comput Biol. 2014; 6: 13-20.
Hafeman, Andrea E., et al. "Injectable Biodegradable Polyurethane Scaffolds with Release of Platelet-derived Growth Factor for Tissue Repair and Regeneration" Pharm Res 2008, Oct. 25(10): 10.1007/s11095-008-9618-z.
Dorati, Rossella, et al. "Biodegradable Scaffolds for Bone Regeneration Combined with Drug-Delivery Systems in Osteomyelitis Therapy" Pharmaceuticals (Basel) Dec. 2017; 10(4): 96.
Martin, John R., et al. "A Porous Tissue Engineering Scaffold Selectively Degraded by Cell-Generated Reactive Oxygen Species" Biomaterials. Apr. 2014 35(12): 3766-3776.

* cited by examiner

*Primary Examiner* — Matthew P Coughlin
(74) *Attorney, Agent, or Firm* — Sorell, Lenna & Schmidt, LLP; William D. Schmidt, Esq.

(57) ABSTRACT

A method of making a hydroxyl-terminated thioketal diol is provided, the method comprising reacting a thioketal ester with a non-pyrophoric reducing agent to form a hydroxyl-terminated thioketal diol. The hydroxyl-terminated thioketal diol can be 2,2-(propane-2,2-diylbis(sulfanediyl)) diethanol. The non-pyrophoric reducing agent can be a sodium aluminum hydride, for example, sodium bis(2-methoxyethoxy) aluminum hydride. The thioketal ester can be dimethyl 2,2-(propane-2,2-diylbis(sulfanediyl)) diacetate. A biodegradable matrix prepared by reacting a hydroxyl-terminated thioketal diol with an isocyanate is provided. A method of making a biodegradable polyurethane composite is also provided.

20 Claims, 8 Drawing Sheets

RD013 TK DIACID DIOL (MDT PROCESS) PROTON NMR

RD046 TK DIESTER DIOL FTIR

RD041 TK DIESTER DIOL BEFORE COLUMN PURIFICATION GC-FID (71.0% PURITY)

RD046 TK DIESTER DIOL GC-FID (87.8% PURITY)

RD046 TK DIESTER DIOL 1H NMR

METHODS OF SYNTHESIS FOR A THIOKETAL DIOL

BACKGROUND

Vertebrate bone is a composite material composed of hydroxyapatite, collagen, and a variety of noncollagenous proteins, as well as embedded and adherent cells. Vertebrate bone can be processed into an implantable biomaterial, such as an allograft, for example, by removing the cells, leaving behind the mineral and extracellular matrix. The processed bone biomaterial can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's bone or may alternatively be processed into soft, moldable or flowable demineralized bone biomaterials that have the ability to induce a cellular healing response.

The use of bone grafts and bone substitute materials in orthopedic medicine is well known. While bone can regenerate without the formation of scar tissue, fractures and other orthopedic injuries take a long time to heal, during which the bone is unable to support physiologic loading. Metal pins, screws, and meshes are frequently required to replace the mechanical functions of injured bone. However, metal is significantly stiffer than bone. Use of metal implants may result in decreased bone density around the implant site due to stress shielding. Furthermore, metal implants are permanent and unable to participate in physiological remodeling.

One attempt to address the limitations resulting from the use of bone graft includes the use of injectable and settable bone cements. For example, poly(methyl methacrylate) (PMMA) bone cements exhibit mechanical properties exceeding those of trabecular bone, and therefore provide mechanical stability to damaged bone. However, PMMA cements are non-resorbable and do not integrate well with host bone. Additionally, while ceramic bone cements are osteoconductive and integrate with host bone, their brittle mechanical properties preclude their use in weight-bearing applications.

Due to the drawbacks associated with settable bone cements, composites of ceramics with resorbable polymers have emerged as an alternative approach that combines the ductile mechanical properties of polymers with the osteoconductivity of ceramics to provide mechanical stability and integration with host bone. Various biodegradable scaffolds made from synthetic polymers have been extensively investigated for use in tissue engineering and regenerative medicine. Examples include poly(lactic-co-glycolic acid) (PLGA), poly(ε-caprolactone) (PCL), polyanhydrides (PAA), and polyurethanes, all of which have a history of use in products approved by the FDA. These materials are useful in a diverse range of regenerative applications because they offer a high degree of tunability, generate a minimal host inflammatory response, and degrade into non-cytotoxic components that are easily cleared from the body.

To attempt to overcome some of these known problems, polyurethane (PUR) (or poly(ester urethane) (PEUR)) scaffolds have been developed that can foam and cure in situ. Such polyurethane scaffolds can comprise polyesters that degrade hydrolytically, and have been shown to have promising properties for treating skin and bone. However, because degradation occurs primarily by acid-catalyzed hydrolysis of ester bonds in the amorphous soft segment, hydroxyl and carboxylic acid end groups are formed. The residual carboxylic acids in the polymer reduce the local pH at later stages of degradation, thereby catalyzing further hydrolysis of the polymer.

Poly(thioketal) polymers are functionalized thioketal crosslinkers used in some cases with polyisocyanates to form biodegradable scaffolds, for example, poly(thioketal) urethane (PTK-UR). Thioketal cross linkers form a functional bond in the application of biodegradable scaffolds. It has been found that unlike PEUR scaffolds, the PTK-UR scaffolds or matrices are more easily degradable by reactive oxygen species (ROS). The PTK-UR composite is a tunable system capable of delivering mechanical and handling properties to meet a range of customer needs. There exists a shortage of suitable biomaterials and scaffolds for tissue engineering. Efforts continue in both soft tissue and bone regeneration to develop cross-linked polyester urethanes for use in biomaterials and scaffolds for tissue engineering. Synthesis of high quality material in high yields utilizing a scalable manufacturing process provides leverage in the development and potential commercialization of new technologies based on this chemistry.

Current manufacturing processes for synthesizing thioketal diols, some of the building blocks of thioketal polymers, are limited in scale and reproducibility and provide low yields.

Moreover, current processes can produce extreme exotherms and toxic gas and require excessive solvent usage. There is therefore a need for efficient methods to synthesize thioketal polymers useful as thioketal crosslinkers for the formation of PTK-UR scaffolds or matrices. There is also a need for providing efficient methods of synthesizing thioketal diols.

SUMMARY

New methods are provided to efficiently and safely make hydroxyl-terminated thioketal diols. In one aspect, the method comprises reacting a thioketal ester with a non-pyrophoric reducing agent to form a hydroxyl-terminated thioketal diol. The hydroxyl-terminated thioketal diol can be 2,2-(propane-2,2-diylbis(sulfanediyl)) diethanol. The non-pyrophoric reducing agent can be a sodium aluminum hydride, for example, sodium bis (2-methoxyethoxy)aluminum hydride. The thioketal ester can be dimethyl 2,2-(propane-2,2-diylbis(sulfanediyl)) diacetate which can be prepared by reacting a thioglycolic acetate with a methoxy functional compound in the presence of bismuth (III) chloride. In some aspects, the thioglycolic acetate is methyl 2-mercaptoacetate and the methoxy functional compound is 2, 2-dimethoxypropane.

In other aspects, a method of making a hydroxyl-terminated thioketal of formula I

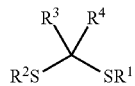

is provided, wherein $R^1$ and $R^2$ are independently $CH_2C(O)OCH_3$ or $CH_2CH_2OH$; and $R^3$ and $R^4$ are independently $CH_3$, $CH_2CH_3$, $(CH_2)_2CH_3$ or $(CH_2)_3CH_3$. The method of making the hydroxyl-terminated thioketal of formula I includes (i) reacting a thioglycolic acetate with a methoxy functional compound in the presence of bismuth (III) chloride to obtain a thioketal ester whenever $R^1$ and $R^2$ are both $CH_2C(O)OCH_3$; and (ii) reacting the thioketal ester with a non-pyrophoric reducing agent to form a hydroxyl-terminated thioketal diol, whenever $R^1$ and $R^2$ are both $CH_2CH_2OH$. In various aspects, (i) the thioglycolic acetate is methyl 2-mercaptoacetate, the methoxy functional compound is 2, 2-dimethoxypropane; (ii) the reducing agent is a sodium aluminum hydride and (iii) the thioketal ester is dimethyl 2,2-(propane-2,2-diylbis(sulfanediyl)) diacetate.

In some embodiments, a biodegradable matrix is provided which is made by reacting a hydroxyl-terminated thioketal diol, the hydroxyl-terminated thioketal diol prepared by reacting a thioketal diester with a non-pyrophoric reducing agent to form a hydroxyl-terminated thioketal diol, with an isocyanate to form the biodegradable matrix. In other embodiments, the biodegradable matrix further comprises a reinforcement material which can include (i) a bone or bone substitutes; or (ii) calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms thereof.

In some embodiments, the isocyanate utilized in preparing the biodegradable matrix includes, without limitations, lysine diisocyanate, lysine triisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates.

In other embodiments, the biodegradable matrix described in this disclosure can further include a bioactive agent, which can comprise an enzyme, organic catalyst, antibiotic, anti-cancer agent, ribozyme, organometallic, protein, glycoprotein, peptide, polyamino acid, antibody, nucleic acid, steroidal molecule, antiviral, antimycotic, anti-cancer agent, analgesic agent, antirejection agent, immunosuppressant, cytokine, carbohydrate, oleophobic, lipid, extracellular matrix and/or its individual component, demineralized bone matrix, mineralized bone, pharmaceutical, chemotherapeutic, cell, virus, siRNA, miRNA, virus vector, prion, or combinations thereof.

In various aspects, there is a method of making a biodegradable polyurethane composite, comprising reacting a hydroxyl-terminated thioketal diol, the hydroxyl-terminated thioketal diol prepared by reacting a thioketal diester with a non-pyrophoric reducing agent to form a hydroxyl-terminated thioketal diol, with an isocyanate and a reinforcement material to form a biodegradable polyurethane composite. In some aspects, the reacting step comprises reacting the hydroxyl-terminated thioketal diol with the isocyanate to form a mixture and mixing the mixture with the reinforcement material to form the biodegradable polyurethane composite. In other aspects, the reacting step comprises exposing the thioketal diol, the polyisocyanate and the reinforcement material to a catalyst. In various aspects, a useful catalyst includes, without limitation, (i) an amine or an organometallic compound; (ii) triethylene diamine, bis(dimethylaminoethyl)ether or dimethylethanolamine; (iii) stannous octoate or dibutyltin laurate; or (iv) iron (III) acetyl acetatonate.

In many aspects, the mixture obtained by reacting the hydroxyl-terminated thioketal diol with the isocyanate includes crosslinked polyurethane.

In various aspects, the reinforcement material used to prepare the biodegradable polyurethane composite includes calcium carbonate, calcium sulfate, calcium phosphosilicate, sodium phosphate, calcium aluminate, calcium phosphate, calcium carbonate, hydroxyapatite, demineralized bone, mineralized bone, or combinations thereof. In other aspects, the method of preparing the biodegradable polyurethane composite discussed in this disclosure further includes adding a bioactive agent to the polyurethane composite.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

DETAILED DESCRIPTION

Figure 1:
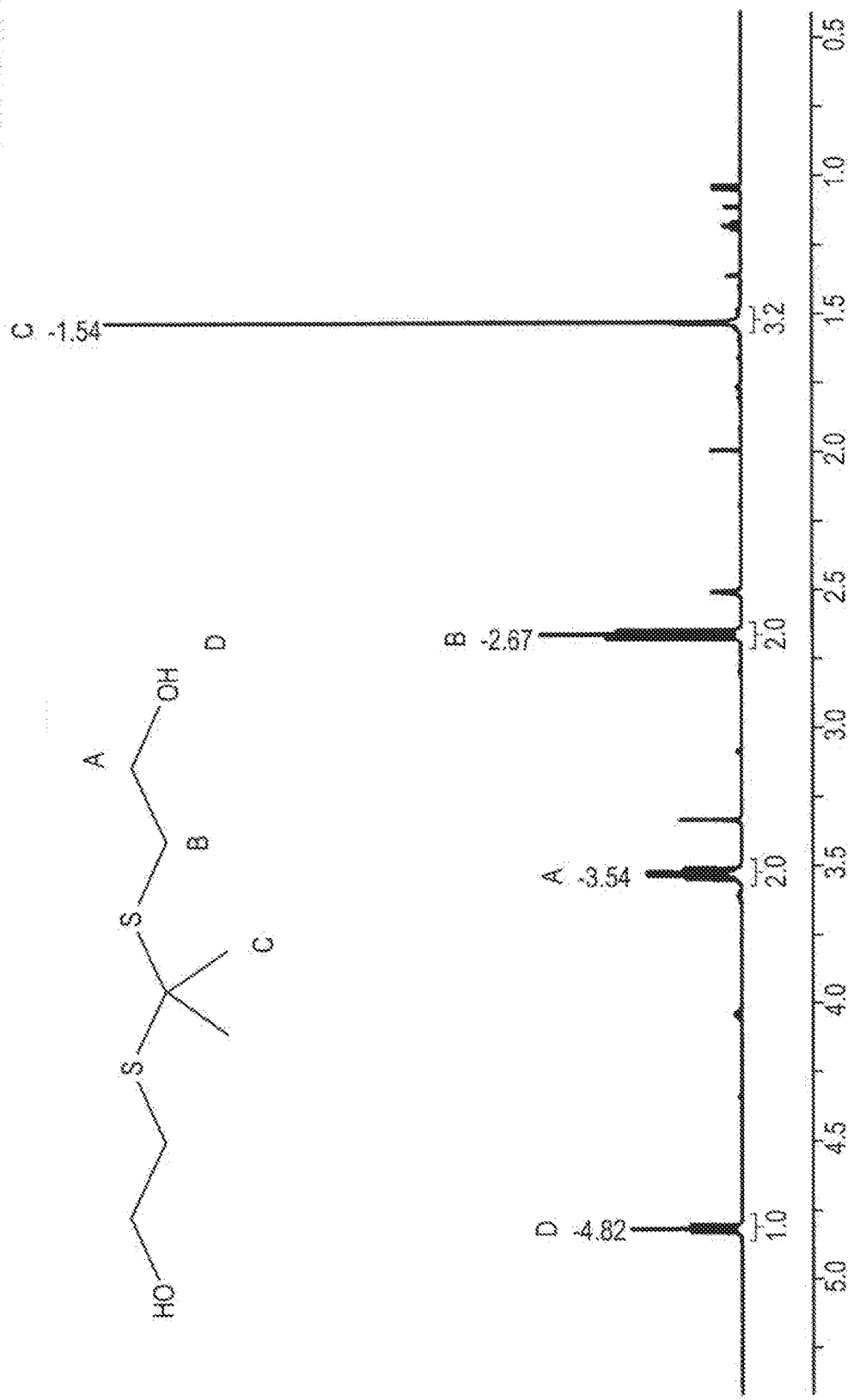
FIG. 1 is a graphic illustration of proton NMR data obtained for thioketal diol prepared by a diacid diol intermediate process (batch RD013)

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an alkanolamine" includes one, two, three or more alkanolamines.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient," "API" or "drug."

The term "biodegradable" includes all or parts of the matrix that will degrade over time by the action of enzymes, by hydrolytic action and/or by other similar mechanisms in the human body. In various embodiments, "biodegradable" includes that the matrix can break down or degrade within the body to non-toxic components as cells (e.g., bone cells) infiltrate the matrix and allow repair of the defect. By "bioerodible" it is meant that the matrix will erode or degrade over time due, at least in part, to contact with substances found in the surrounding tissue, fluids or by cellular action. By "bioabsorbable" it is meant that the matrix will be broken down and absorbed within the human body, for example, by a cell or tissue. "Biocompatible" means that the matrix will not cause substantial tissue irritation or necrosis at the target tissue site and/or will not be carcinogenic.

The term "bioactive agent" or "biologically active agent" is used herein to refer to compounds or entities that alter, promote, speed, prolong, inhibit, activate, or otherwise affect biological or chemical events in a subject (e.g., a human). For example, bioactive agents may include, but are not limited to osteogenic, osteoinductive, and osteoconductive agents, anti-HIV substances, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-Parkinson agents, anti-spasmodics and muscle contractants including channel blockers, miotics and anti-cholinergics, anti-glaucoma compounds, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotics, targeting agents, chemotactic factors, receptors, neurotransmitters, proteins, cell response modifiers, cells, peptides, polynucleotides, viruses, and vaccines. In certain embodiments, the bioactive agent is a drug. In certain embodiments, the bioactive agent is a small molecule.

Antimicrobial used as bioactive agents in embodiments of the present invention may be selected from one that does little to no harm to the healing process. Clinically, antibiotics may be selected for their spectrum or ease of administration to the patient. When selecting an antibiotic for local delivery, the physical characteristics (charge and hydrophobicity) and state (liquid or powder) of the drug may also be considered. Additionally, antimicrobials' effects on eukaryotic cells may be considered when developing an embodiment of the present invention, including a dual-delivery scaffold embodiment. In vitro studies that evaluated the effect of eight concentrations (ranging from 0 to 5,000 mg/ml) of 21 antibiotics on the viability and activity of osteoblasts found that vancomycin, a tricyclic glycopeptide antibiotic that is efficacious for treating infections caused by gram-positive bacteria such as Staph. aureus, may have the least detrimental effects on osteoblast function. All other antibiotics in the study reduced the alkaline phosphatase (ALP) activity at doses that were 10-50 times lower than that of vancomycin. Other studies also indicate that vancomycin has less adverse effects on osteoblasts than other commonly used antibiotics in vitro. Furthermore, vancomycin may not impede bone growth in fractures in vivo. Some embodiments comprise an antibiotic selected from the group consisting of clindamycin, cefazolin, oxacillin, rifampin, trimethoprim/sulfamethoxazole, vancomycin, ceftazadime, ciprofloxacin, colistin, and imipenem.

A more complete listing of bioactive agents and specific drugs suitable for use in the present invention may be found in *Pharmaceutical Substances. Syntheses, Patents, Applications*, by Axel Kleemann and Jurgen Engel, Thieme Medical Publishing, 1999; *Merck Index: An Encyclopedia of Chemicals, Drugs, and Biologicals*, Edited by Susan Budavari et al., CRC Press, 1996; *United States Pharmacopeia*-25/ *National Formulary*-20, published by the United States Pharmcopeial Convention, Inc., Rockville Md., 2001; and *Pharmazeutische Wirkstoffe*, edited by Von Keemann et al., Stuttgart/New York, 1987, all of which are incorporated herein by reference. Drugs for human use listed by the U.S. Food and Drug Administration (FDA) under 21 C.F.R. §§ 330.5, 331-361 and 440-460, and drugs for veterinary use listed by the FDA under 21 C.F.R. §§ 500-589, all of which are incorporated herein by reference, are also considered acceptable for use in accordance with the present invention.

The term "biocompatible" as used herein, is intended to describe materials that, upon administration in vivo, do not induce undesirable side effects. In some embodiments, the material does not induce irreversible, undesirable side effects. In certain embodiments, a material is biocompatible if it does not induce long term undesirable side effects. In certain embodiments, the risks and benefits of administering a material are weighed in order to determine whether a material is sufficiently biocompatible to be administered to a subject.

The term "biomolecules" as used herein, refers to classes of molecules (e.g., proteins, amino acids, peptides, polynucleotides, nucleotides, carbohydrates, sugars, lipids, nucleoproteins, glycoproteins, lipoproteins, steroids, natural products, etc.) that are commonly found or produced in cells, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active fragments or subunits. In some embodiments, the biomolecule is a growth factor, chemotactic factor, cytokine, extracellular matrix molecule, or a fragment or derivative thereof, for example, a cell attachment sequence such as a peptide containing the sequence, arginylglycylaspartic acid (RGD).

The term "carbohydrate" as used herein, refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula CnH2nOn. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates may exist in many different forms, for example, conformers, cyclic forms, acyclic forms, stereoisomers, tautomers, anomers, and isomers.

The term "composite" as used herein, is used to refer to a unified combination of two or more distinct materials. The composite may be homogeneous or heterogeneous. For example, a composite may be a combination of bone particles and a polymer; a combination of bone particles, polymers and antibiotics; or a combination of two different polymers. In certain embodiments, the composite has a particular orientation.

The term "contacting" refers to any method of providing or delivering a scaffold on, to or near the tissue to be treated. Such methods are described throughout this document and include injection of a biodegradable scaffold onto a tissue wound and/or molding a biodegradable scaffold in a mold and then placing the molded scaffold on a tissue wound. In some embodiments contacting refers to completely covering a skin wound and optionally, the surrounding skin, with a biodegradable polyurethane scaffold. In some embodiments contacting refers to placing a biodegradable polyurethane scaffold between two or more bone fragments that have fractured. In various aspects, a scaffold can be in contact with an existing tissue wound and, in further various aspects, a polyurethane scaffold can be contacted prophylactically, that is, to prevent a wound from forming on tissue.

The term "flowable polymer material" as used herein, refers to a flowable composition including one or more of monomers, prepolymers, oligomers, low molecular weight polymers, uncross-linked polymers, partially cross-linked polymers, partially polymerized polymers, polymers, or combinations thereof that have been rendered formable. One skilled in the art will recognize that a flowable polymer material need not be a polymer but may be polymerizable. In some embodiments, flowable polymer materials include polymers that have been heated past their glass transition or melting point. Alternatively, or in addition, a flowable polymer material may include a partially polymerized polymer, telechelic polymer, or prepolymer. A prepolymer is a low molecular weight oligomer typically produced through step growth polymerization. The prepolymer is formed with an excess of one of the components to produce molecules that are all terminated with the same group. For example, a diol and an excess of a diisocyanate may be polymerized to produce isocyanate terminated prepolymer that may be combined with a diol to form a polyurethane. Alternatively, or in addition, a flowable polymer material may be a polymer material/solvent mixture that sets when the solvent is removed.

The term "nontoxic" is used herein to refer to substances which, upon ingestion, inhalation, or absorption through the skin by a human or animal, do not cause, either acutely or chronically, damage to living tissue, impairment of the central nervous system, severe illness or death.

The term "osteoconductive" as used herein, refers to the ability of a substance or material to provide surfaces which are receptive to the growth of new bone.

The term "osteogenic" as used herein, refers to the ability of a substance or material that can induce bone formation.

The term "osteoinductive" as used herein, refers to the quality of being able to recruit cells (e.g., osteoblasts) from the host that have the potential to stimulate new bone formation. In general, osteoinductive materials are capable of inducing heterotopic ossification, that is, bone formation in extraskeletal soft tissues (e.g., muscle).

The term "osteoimplant" is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site, e.g., one resulting from injury, a defect brought about during surgery, infection, malignancy, inflammation, or a developmental malformation. Osteoimplants can be used in a variety of orthopedic, neurosurgical, dental, and oral and maxillofacial surgical procedures such as the repair of simple and compound fractures and non-unions, external, and internal fixations, joint reconstructions such as arthrodesis, general arthroplasty, deficit filling, disectomy, laminectomy, anterior cerival and thoracic operations, spinal fusions, etc.

The terms "polynucleotide," "nucleic acid," or "oligonucleotide" as used herein, refer to a polymer of nucleotides. The terms "polynucleotide," "nucleic acid," and "oligonucleotide" may be used interchangeably. Typically, a polynucleotide comprises at least three nucleotides. DNAs and RNAs are exemplary polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thithymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose) or modified phosphate groups (e.g., phosphorothioates and 5'-N-phosphoramidite linkages). The polymer may also be a short strand of nucleic acids such as RNAi, siRNA, or shRNA.

The terms "polypeptide," "peptide," or "protein," as used herein, include a string of at least three amino acids linked together by peptide bonds. The terms "polypeptide," "peptide," and "protein," may be used interchangeably. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide or the incorporation of D-amino acids, etc. None of the modifications should substantially interfere with the desired biological activity of the peptide.

The terms "polysaccharide" or "oligosaccharide" as used herein, refer to any polymer or oligomer of carbohydrate residues. Polymers or oligomers may consist of anywhere from two to hundreds to thousands of sugar units or more. "Oligosaccharide" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose) and fructose. In some embodiments, glycosaminoglycans are considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "porogen," as used herein, refers to a chemical compound that may be part of the inventive composite and upon implantation/injection or prior to implantation/injection diffuses, dissolves and/or degrades to leave a pore in the osteoimplant composite. A porogen may be introduced into the composite during manufacture, during preparation of the composite (e.g., in the operating room) or after implantation/injection. A porogen essentially reserves space in the composite while the composite is being molded, but once the composite is implanted the porogen diffuses, dissolves, or degrades, thereby inducing porosity into the composite. In this way, porogens provide latent pores. In certain embodiments, the porogen may be leached out of the composite before implantation/injection. This resulting porosity of the implant generated during manufacture or after implantation/injection (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogens can also be natural or synthetic polymers, oligomers, or monomers that are water soluble or degrade quickly under physiological conditions. Exemplary polymers include polyethylene glycol, poly(vinylpyrollidone), pullulan, poly(glycolide), poly(lactide), poly(lactide-co-glycolide), other polyesters, and starches. In certain embodiments, bone particles utilized in provided composites or compositions may act as porogens. For example, osteoclasts resorb allograft and make pores in composites.

In some embodiments, porogens may refer to a blowing agent (i.e., an agent that participates in a chemical reaction to generate a gas). Water may act as such a blowing agent or porogen.

The term "porosity" as used herein, refers to the average amount of non-solid space contained in a material (e.g., a composite of the present invention). Such space is considered void of volume even if it contains a substance that is liquid at ambient or physiological temperature, e.g., 0.5° C. to 50° C. Porosity or void volume of a composite can be defined as the ratio of the total volume of the pores (i.e., void volume) in the material to the overall volume of composites.

In some embodiments, porosity, defined as the volume fraction of pores, can be calculated from composite foam density, which can be measured gravimetrically. Porosity may in certain embodiments refer to "latent porosity" wherein pores are only formed upon diffusion, dissolution, or degradation of a material occupying the pores. In such an instance, pores may be formed after implantation/injection. It will be appreciated by those of ordinary skill in the art that the porosity of a provided composite or composition may change over time, in some embodiments, after implantation/injection (e.g., after leaching of a porogen, when osteoclasts resorbing allograft bone, etc.). For the purpose of the present disclosure, implantation/injection may be considered as "time zero" ($T_0$). In some embodiments, the present invention provides composites and/or compositions having a porosity of at least about 30%, at least about 40%, at least about 50%, at least about 60%, at least about 70%, at least about 80%, at least about 90% or more than 90%, at time zero. In certain embodiments, pre-molded composites and/or compositions may have a porosity of at least about 30%, at least about 40%, at least about 50%, at least about 60%, at least about 70%, at least about 80%, at least about 90% or more than 90%, at time zero. In certain embodiments, injectable composites and/or compositions may have a porosity of as low as 3% at time zero. In certain embodiments, injectable composites and/or compositions may cure in situ and have a porosity of at least about 30%, at least about 40%, at least about 50%, at least about 60%, at least about 70%, at least about 80%, at least about 90% or more than 90% after curing.

The term "remodeling" as used herein, describes the process by which native bone, processed bone allograft, whole bone sections employed as grafts, and/or other bony tissues are replaced with new cell-containing host bone tissue by the action of osteoclasts and osteoblasts. Remodeling also describes the process by which non-bony native tissue and tissue grafts are removed and replaced with new, cell-containing tissue in vivo. Remodeling also describes how inorganic materials (e.g., calcium-phosphate materials, such as β-tricalcium phosphate) are replaced with living bone.

The term "scaffold" or "matrix" as used herein refers to a substance that can be used to treat tissue and/or a wound. In some embodiments the scaffold or graft is a foam that can be injected between fractured bone fragments to help heal the fracture. In some embodiments the scaffold or graft is a material that can be placed on or near tissue to be treated. The terms "composite," "scaffold," "matrix" and "graft" may be used interchangeably herein to refer to embodiments of the presently-disclosed subject matter.

The term "setting time" as used herein, is approximated by the tack-free time (TFT), which is defined as the time at which the material could be touched with a spatula with no adhesion of the spatula to the foam. At the TFT, the wound could be closed without altering the properties of the material.

The term "shaped" as used herein, is intended to characterize a material (e.g., composite) or an osteoimplant refers to a material or osteoimplant of a determined or regular form or configuration in contrast to an indeterminate or vague form or configuration (as in the case of a lump or other solid matrix of special form). Materials may be shaped into any shape, configuration, or size. For example, materials can be shaped as sheets, blocks, plates, disks, cones, pins, screws, tubes, teeth, bones, portions of bones, wedges, cylinders, threaded cylinders, and the like, as well as more complex geometric configurations.

The term "small molecule" as used herein, is used to refer to molecules, whether naturally-occurring or artificially created (e.g., via chemical synthesis), that have a relatively low molecular weight. In some embodiments, small molecules have a molecular weight of less than about 2,500 g/mol, for example, less than 1000 g/mol. In certain embodiments, small molecules are biologically active in that they produce a local or systemic effect in animals, such as mammals, e.g., humans. In certain embodiments, a small molecule is a drug. In certain embodiments, though not necessarily, a drug is one that has already been deemed safe and effective for use by an appropriate governmental agency or body (e.g., the U.S. Food and Drug Administration).

The terms "subject" or "subject in need thereof" refer to a target of administration, which optionally displays symptoms related to a disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote an age or sex. Thus, adult and newborn subjects, as well as fetuses, whether male or female, are intended to be covered. A patient refers to a subject afflicted with a disease or disorder. The term "patient" includes human and veterinary subjects.

The term "tissue" is used herein to refer to a population of cells, generally consisting of cells of the same kind that perform the same or similar functions. The types of cells that make the tissue are not limited. In some embodiments, tissue is part of a living organism and in some embodiments, tissue is tissue excised from a living organism or artificial tissue. In some embodiments tissue can be part of skin, bone, an organ or the like.

The term "transformation" as used herein, describes a process by which a material is removed from an implant site and replaced by host tissue after implantation. Transformation may be accomplished by a combination of processes, including but not limited to remodeling, degradation, resorption, and tissue growth and/or formation. Removal of the material may be cell-mediated or accomplished through chemical processes, such as dissolution and hydrolysis.

The terms "treatment" or "treating" refer to the medical management of a patient with the intent to heal, cure, ameliorate, stabilize, or prevent a disease, pathological condition, or disorder. This term includes active treatment, that is, treatment directed specifically toward the improvement of a disease, pathological condition, or disorder, and includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. For example, in some embodiments treatment refers to the healing bone tissue that is fractured and/or healing wounded skin tissue.

The term "wound" as used herein refers to any defect, injury, disorder, damage, or the like of tissue. In some embodiments a wound can be a bone fracture. In some embodiments a wound is damaged skin or skin that must heal from a particular disorder.

The term "polyurethane" and "PUR" as used herein, is intended to include all polymers incorporating more than one urethane group (—NH—CO—O—) in the polymer backbone. Polyurethane materials, in some embodiments, refer to the compositions formed by the reaction of a polyisocyanate (such as a triisocyanate) and a polyol (such as a diol) or polyamine, optionally with any additional components. In some embodiments, the polyamine can react with the polyisocyanate to form a polyurea. Typical reaction to form a polyurethane is shown below, where R1 and R2 are alkyl moieties:

HO—R$_1$—OH + OCN—R$_2$—NCO ⟶

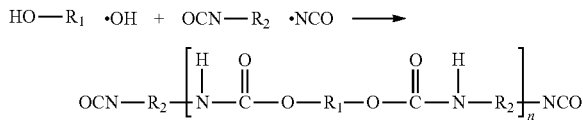

The term "polyisocyanate," as that term is used herein, encompasses any chemical structure comprising two or more isocyanate groups. A "diisocyanate," as used herein, is a subset of the class of polyisocyanates, a chemical structure containing two isocyanate (—OCN) groups. A "triisocyanate," as used herein, is a subset of the class of polyisocyanates, a chemical structure containing three isocyanate (—OCN) groups. Similarly, a "polyol" contains two or more alcohol (—OH) groups, while a "diol" contains two alcohol groups, and a "polyamine" contains two or more amine groups (e.g., primary amine groups).

The polyurethane or polyurea can contain growth factors. As used herein, "growth factors" are chemicals that regulate cellular metabolic processes including, but not limited to, differentiation, proliferation, synthesis of various cellular products, and other metabolic activities. Growth factors may include several families of chemicals including, but not limited to, cytokines, eicosanoids, and differentiation factors, such as, for example, platelet-derived growth factor (PDGF). Other factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein. Other growth factors include GDF-5, the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenic proteins including all BMPs including, but not limited to, BMP-2, BMP-4, and BMP-7.

The polyurethane or polyurea can be "osteogenic," where it can enhance or accelerate the ingrowth of new bone tissue by one or more mechanisms such as osteogenesis, osteoconduction and/or osteoinduction.

In some embodiments, polyurethane materials refer to the compositions formed from the reaction of a polyisocyanate (such as a triisocyanate) and a polyol (such as a diol) and optionally, a catalyst.

Reference will now be made in detail to certain embodiments of the invention, examples of which are illustrated in the accompanying drawings. While this disclosure will be described in conjunction with the illustrated embodiments, it will be understood that they are not intended to limit this application to those embodiments.

Methods for Making Thioketal Diols

Aspects of this application include preparing functionlized thioketal crosslinkers for use with polyisocyantate to form biodegradable scaffolds or matrices. In some embodiments, the biodegradable matrices include poly(thioketal-urethane) (PTK-UR) tissue scaffolds. In some embodiments the scaffolds comprise a polythioketal polymer and polyisocyanates. Exemplary scaffolds can be used to treat tissue. Other exemplary scaffolds can be used as delivery systems for biologically active agents to promote tissue healing and regeneration.

Some embodiments of the presently-disclosed subject matter relate to scaffolds or matrices that can be used in various clinical applications, for example, as bone void fillers, to repair or help healing of skeletal deficiencies resulting from trauma, tumors, surgery, iatrogenic, congenital, genetic, metabolic and degenerative or abnormal development, and inflammatory infection. In some embodiments, scaffolds promote cellular infiltration from adjacent osseous tissues, thus accelerating the remodeling process. In some embodiments scaffolds aid in the treatment of cutaneous wounds.

Synthetic polymers can be designed with properties targeted for a given clinical application. For example, polyurethanes (PUR) are a useful class of biomaterials due to the fact that they can be injectable or moldable as a reactive liquid that subsequently cures to form a porous composite.

In some aspects, polyurethanes can be made by reacting together a polyisocyanate and a component having two or more hydroxyl groups (i.e., polyols). The PTK-UR scaffolds described herein are the product of the reaction between at least two components, namely a polyisocyanate and a hydroxyl-terminated thioketal or a polythioketal polymer, which can be a copolymer. Polyisocyanates, hydroxyl-terminated TKs, and/or PTK polymers can be selected to produce polymers having various physiochemical properties and morphologies including, for example, flexible foams, rigid foams, elastomers, coatings, adhesives, and sealants. In other aspects, other biocompatible and/or biodegradable polymers may be used with the present scaffolds.

In various embodiments, the polyisocyanate is combined with a hydroxyl-terminated TK to formulate the poly(thioketal urethane) (PTKUR). The thioketal includes any hydroxyl-terminated thioketal with a functionality of 2 or more, including, but not limited to, for example, thioketal diols. In one embodiment, the TKs are low molecular weight TK. As used herein, the term "low molecular weight" refers to compounds having an equivalent weight (i.e., molecular weight/functionality) of less than 500 grams/equivalent (g/eq), between 25 and 500 g/eq, less than 300 g/eq, between 25 and 300 g/eq, less than 150 g/eq, between 25 and 150 g/eq, between 50 and 150 g/eq, between 75 and 150 g/eq, between 90 and 150 g/eq, or any combination, sub-combination, range, or sub-range thereof. In another embodiment, the TK includes an equivalent weight of between 75 and 125 g/eq, such as, but not limited to, an equivalent weight of about 100 g/eq. In a further embodiment, for example, TK includes the formula:

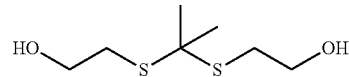

In certain embodiments, synthesizing the hydroxyl-terminated TK includes reacting thioglycolic acid with a methoxy functional molecule to form a carboxyl end functional intermediate, followed by reduction of the carboxyl end functional intermediate with any suitable reducing agent, such as lithium aluminum hydride, to form a hydroxyl functional TK. For example, as shown below in Scheme 1, one method of synthesizing a low molecular weight TK diol includes reaction of thioglycolic acid and 2,2-dimethoxypropane to form a carboxyl-terminated TK, followed by reduction with lithium aluminum hydride to form the hydroxyl-terminated TK diol.

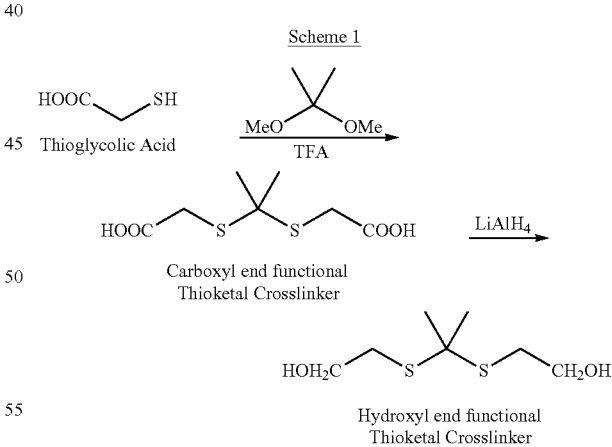

In another embodiment, the thioglycolic acid can be 2-mercaptoacetic acid which is reacted with 2,2-dimethoxypropane in the presence of bismuth (III) chloride to form the diacid 2,2-(propane-2,2-diylbis(sulfanediyl)) diacetic acid. Subsequently, this thioketal diacid intermediate is reacted with a reducing agent such as lithium aluminum hydride ($LiAlH_4$) to form the hydroxyl-terminated thioketal diol monomer 2,2-(propane-2,2-diylbis(sulfanediyl)) diethanol as illustrated in Scheme 2.

Scheme 2

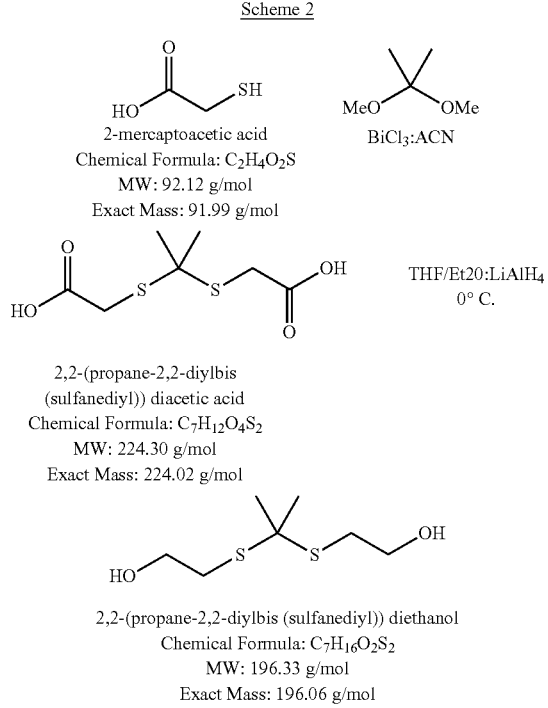

Figure 2:
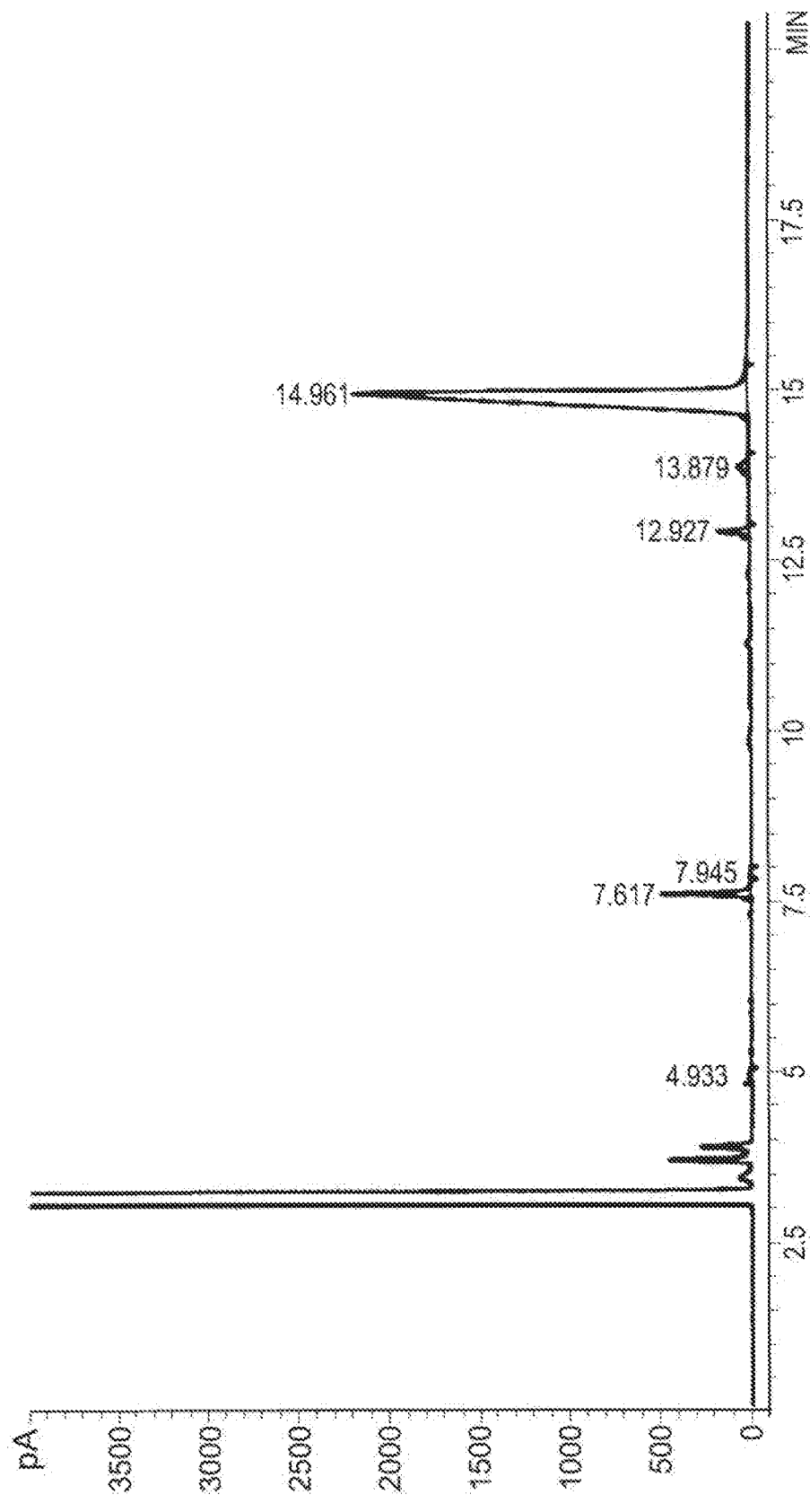
FIG. 2 is a graphic illustration of gas chromatography flame ionization detector (GC-FID) for thioketal diol prepared by a diacid diol intermediate process (batch RD13)
Figure 3:
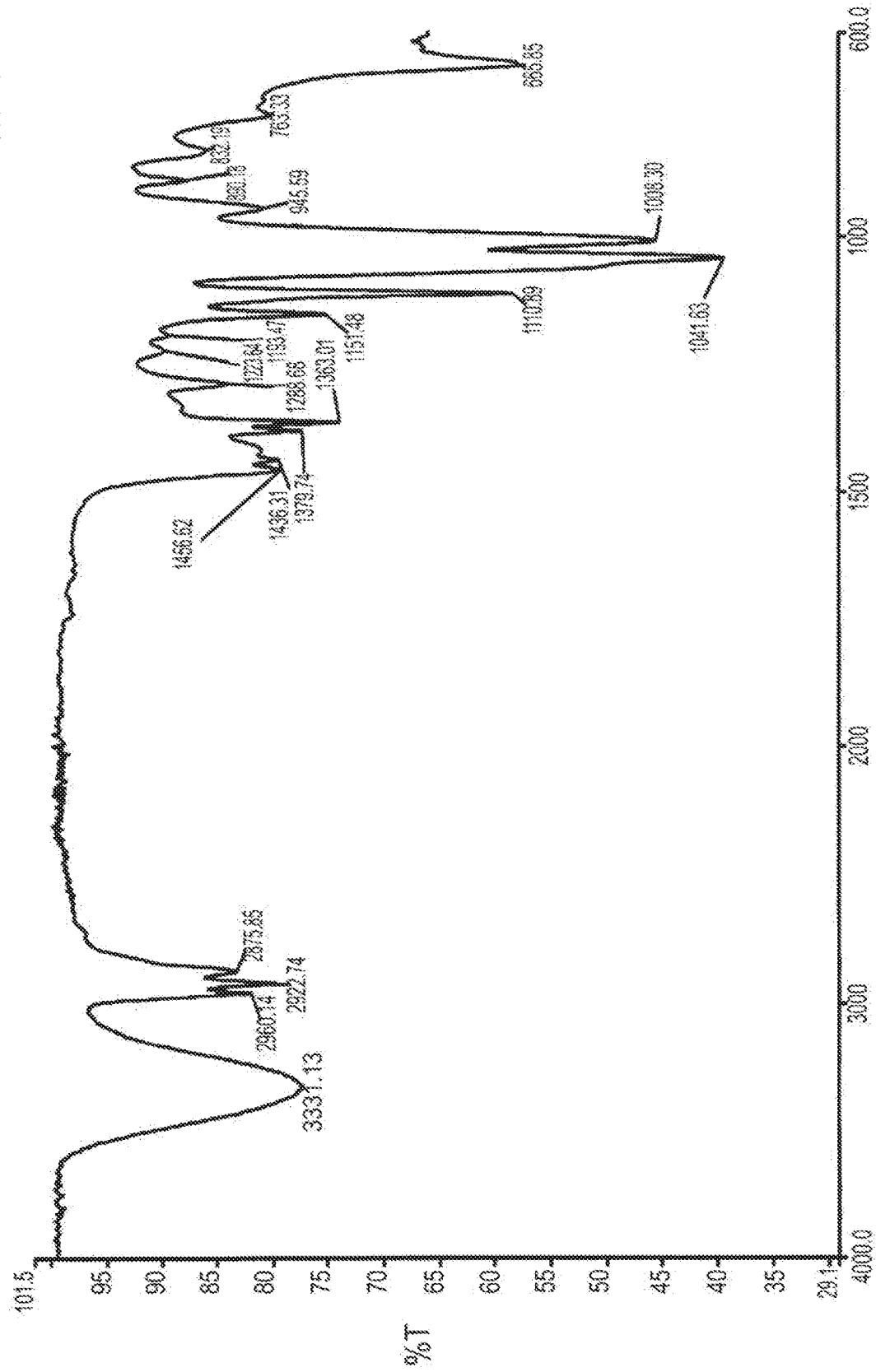
FIG. 3 is a graphic illustration of Fourier-transform infrared (FTIR) data obtained for tioketal diol prepared by a thioketal diester intermediate process (batch RD046)

In other embodiments, thioketal diols are obtained by using correct stoichiometric ratios in the absence of diethyl ether and sodium hydroxide, a process in which the diacid intermediate is a light-yellow solid resulting in reduced solvent volume, increased safety and increased yield and purity. Results of TK diols obtained by a diacid intermediate are illustrated in FIGS. 1 and 2. FIG. 1 illustrates a proton NMR (batch RD013) while FIG. 2 illustrates a GC-FID for the same batch.

According to another embodiment, the hydroxyl terminated thioketal diol can be provided by another synthetic route where the thioketal diol is prepared from a thioketal diester intermediate. This synthetic process is illustrated in Scheme 3.

Scheme 3

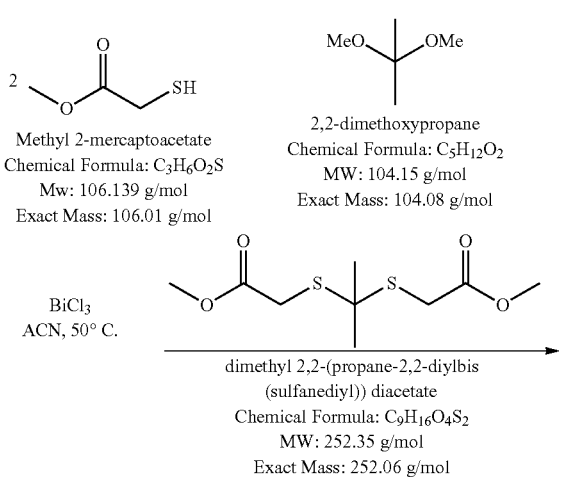

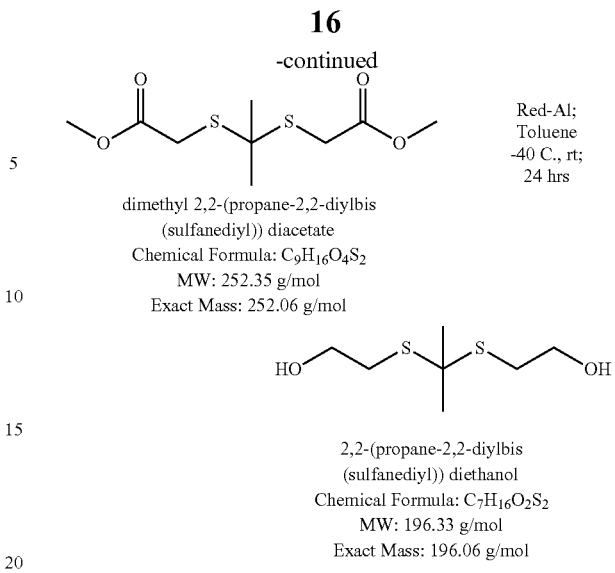

The synthetic process to form thioketal diol is a two-step process where a thioketal intermediate is formed by esterification. In step two, the intermediate is reduced to thioketal diol. In the first step a thyoglicolic ester, for example, methyl 2-mercaptoacetate is reacted with 2,2-dimethoxy propane in the presence of bismuth (III) chloride as a catalyst and acetonitrile at 50° C. to provide a diester, namely dimethyl 2,2-(propane-2,2-diylbis(sulfanediyl)) diacetate.

The second step is a reduction step where lithium aluminum hydride (LiAlH$_4$) is replaced with Red-Al, whose chemical name is sodium bis(2-methoxyethoxy) aluminum hydride (NaAlH$_2$(OCH$_2$CH$_2$OCH$_3$)$_2$). LiAlH$_4$ has a flash point of −25° C., is highly reactive and may be handled with a full-face respirator or multipurpose combination respirator due to respiratory sensitization and reproductive toxicity along with many other health hazards. Lithium aluminum hydride also has a short shelf-life and exhibits limited solubility being soluble primarily in ethers. By contrast, Red-Al is non-pyrophoric at room temperature and although it can react exothermically, it typically does not ignite. Nevertheless, engineering controls such as a fume hood are indicated for use. Red-Al offers good solubility in many organic solvents, for example, aromatic solvents such as toluene. This allows the amount of reducing agent utilized in the synthesis of hydroxyl-terminated thioketal diol to be lowered from 1 L of LiAlH$_4$ to 350 g Red-Al. The number of steps needed for the reduction is reduced about 42% by removing the washing steps and drying step. The resulting diester intermediate is a liquid that is easy to be carried into the next step without additional workup. It has also been shown to have higher purity by NMR. In some aspects, a 5 L reaction yields 90 grams of product compared to 30 grams of product which correlates to about a 70% increase in yield at this batch size.

In other embodiments, the crude TK diol obtained by the diester reduced by Red-Al synthetic route is purified on a silica gel column as described in more detail in the examples below. Purities of about 85%, 88% and about 90% of TK diol were achieved.

Figure 6:
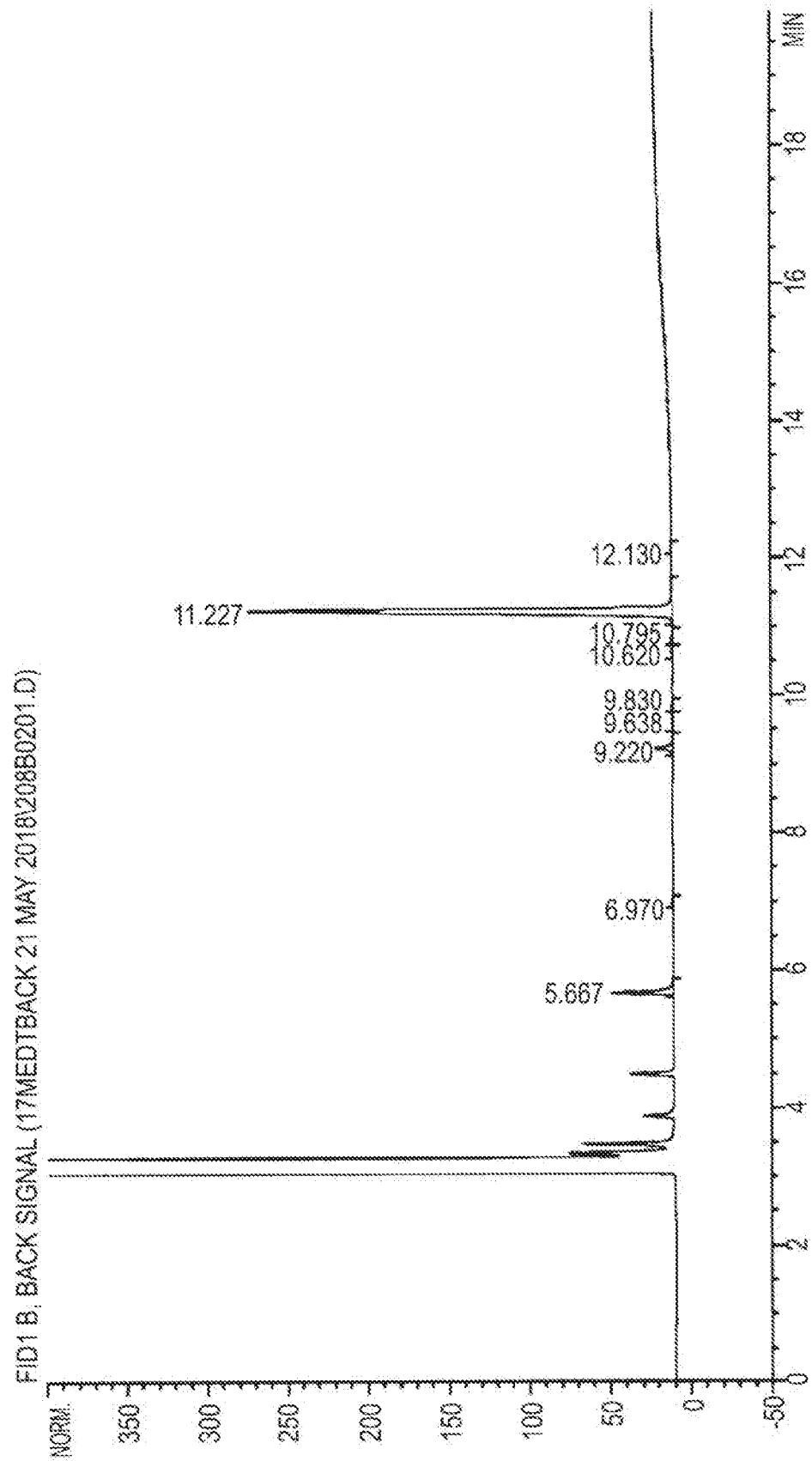
FIG. 6 is a graphic illustration of GC-FID data obtained for tioketal diol prepared by a diester intermediate process yielding 87.8% purity (batch RD046)
Figure 7:
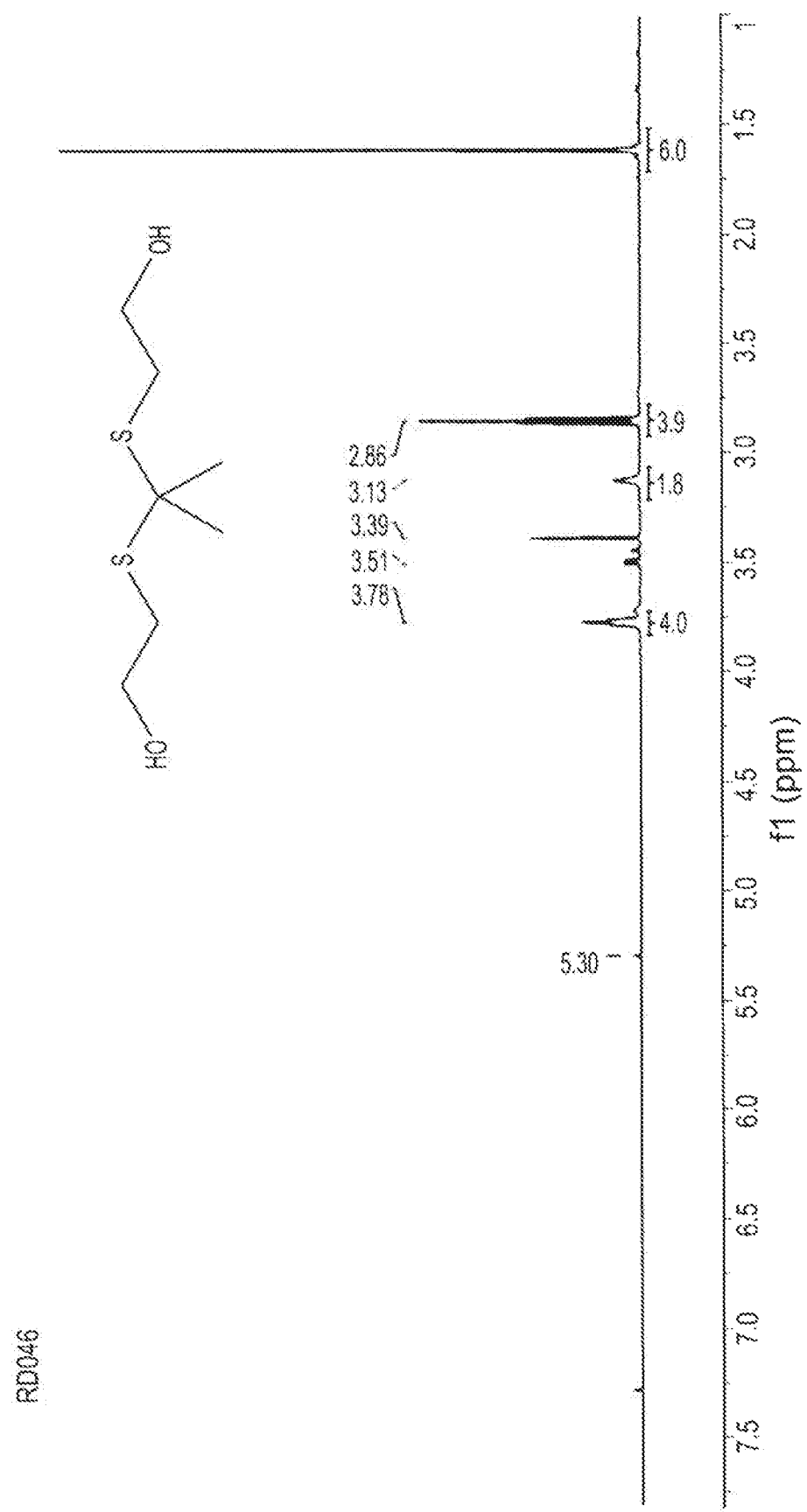
FIG. 7 is a graphic illustration of proton NMR data obtained for thioketal diol in DMSO prepared by a thioketal diester intermediate process (batch RD046)
Figure 8:
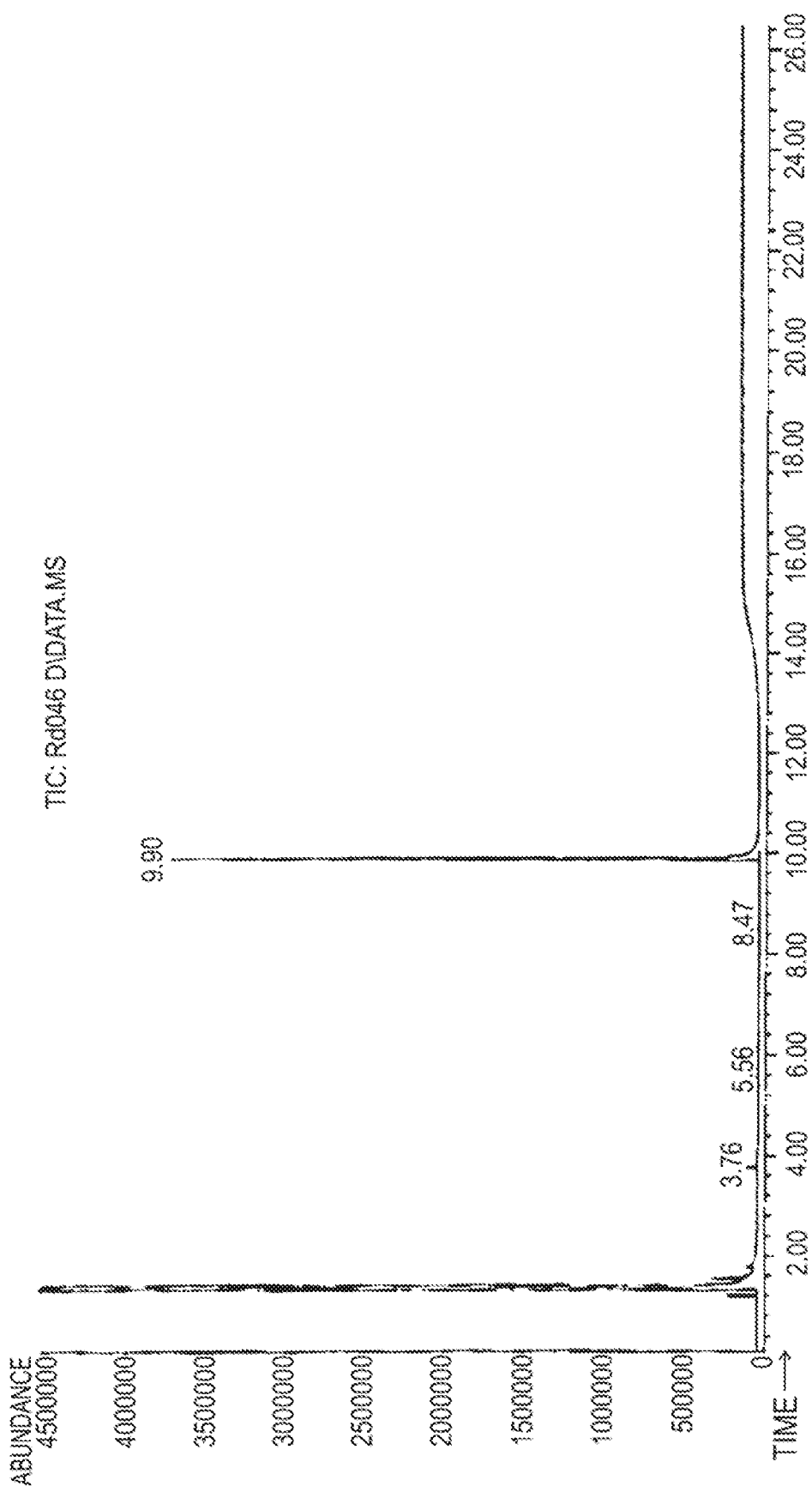
FIG. 8 is a graphic illustration of GC-MS data obtained for thioketal diol prepared by a diester intermediate process yielding 95.3% purity (batch RD046).

High purity samples of TK diol obtained via a diester intermediate process are illustrated in FIGS. 6 and 8. FIG. 6 illustrates GC-FID data for TK diol prepared by a diester intermediate process yielding 87.8% purity (batch RD046). FIG. 8 is GC-MS data obtained for thioketal diol prepared by a diester intermediate process yielding 95.3% purity (batch RD046).

A comparison of yields obtained for TK diol and its intermediates prepared by reducing a diacid with LiAlH$_4$ and a diester reduced with Red-Al is illustrated in Table 1 below.

TABLE 1

|  | Diacid Route | Diester Route |
|---|---|---|
| Overall process yield | 14 | 38 |
| Step 1 yield (coupling) | 32 | 99 |
| Step 2 yield (reduction) | 43 | 50 |
| Purification | — | 80 |

The superiority of preparing TK diols by the diester reduced with Red-Al process was also confirmed by subjecting TK diols obtained by the diacid route and the diester route to Fourier transform infrared spectroscopy (FTIR) and gas chromatography flame ionization detector (GC-FID) as illustrated in FIGS. 2, 3, 4, 5, 6, 7 and 8.

In various embodiments, in the two-step process based on a diester intermediate, anhydrous 2-methyltetrahydrofuran (Me-THF) was replaced with tetrahydrofuran, LiAlH$_4$ was replaced with Red-Al in toluene and diluted with anhydrous toluene. Further, the reduction was quenched with Me-THF/isopropyl alcohol, KOH in methanol/water (50:50 v:v). These changes resulted in a process having increased safety, efficiency obtained by minimizing the number of process steps, reduces waste and water use, increased manufacturability, yield and purity of product.

Polyisocyanates

As described above, the PTK-UR scaffolds described herein are the product of a reaction between at least two components, namely a polyisocyanate and a hydroxyl-terminated thioketal or a polythioketal polymer, which can be a copolymer.

thereof. In some embodiments, hexamethylene diisocyanate (HDI) trimer (HDIt) sold as Desmodur N3300A may be a polyisocyanate utilized in the present disclosure. In some embodiments, polyisocyanates used in the present invention includes approximately 10 to 55% NCO by weight (wt % NCO=100*(42/Mw)). In some embodiments, polyisocyanates include approximately 15 to 50% NCO.

Useful polyisocyanates also include aromatic polyisocyanates. In one aspect, methods of making polyisocyanates are described in U.S. Pat. No. 9,266,824, incorporated herein in its entirety.

Poly(Thioketal Urethane)

Polyurethanes can be made by reacting together the components of a two-component composition, one of which includes a polyisocyanate and a polyol, in this application a hydroxyl-terminated thioketal (TK) diol. It is to be understood that by "a two-component composition" it means a composition comprising two essential types of polymer components. In some embodiments, such a composition may additionally comprise one or more other optional components.

Depending on reaction conditions, a product of reacting an isocyanate with a polyol can be a polymer that is fully polymerized, or a prepolymer that can be further polymerized. In some embodiments, a prepolymer produced from an isocyanate is used in a two-component composition to make polyurethane materials. A prepolymer is a low molecular weight oligomer typically produced through stepwise growth polymerization. For example, a polyol and an excess of polyisocyanate may be polymerized to produce isocyanate terminated prepolymer that may be combined with a polyol to form a polyurethane.

A TK diol prepared according to the processes discussed in this disclosure was reacted with a 2.5 molar excess of LTI to form an LTI-TK prepolymer as illustrated below:

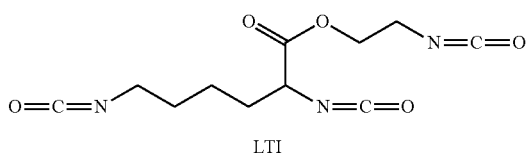

Thioketal

LTI

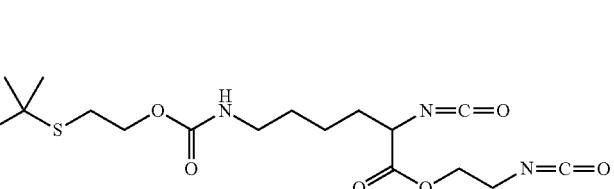

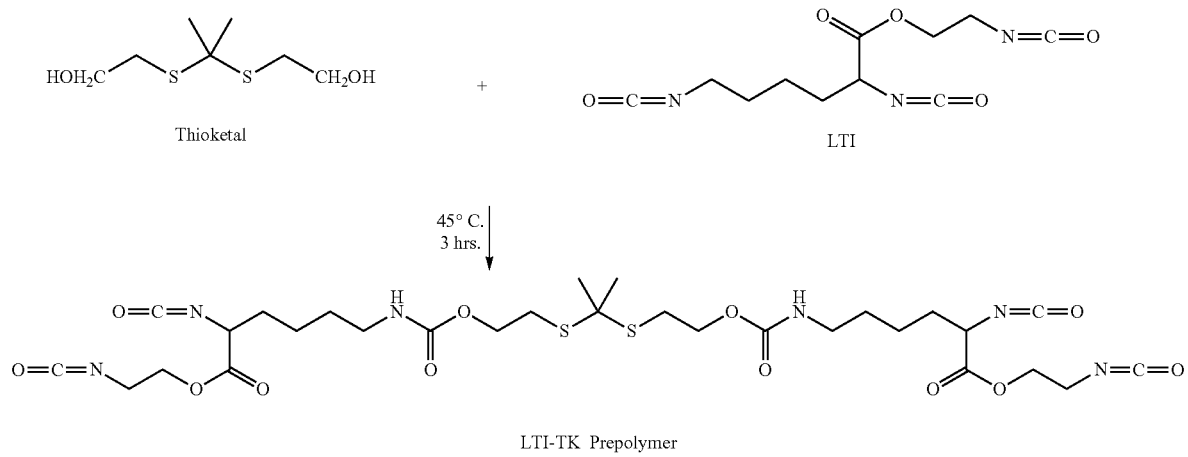

LTI-TK Prepolymer

Polyisocyanates or multi-isocyanate compounds for use in the present disclosure include aliphatic polyisocyanates. Exemplary aliphatic polyisocyanates include, but are not limited to, lysine diisocyanate, an alkyl ester of lysine diisocyanate (for example, lysine methyl ester diisocyanate (LDI)), lysine triisocyanate (LTI), hexamethylene diisocyanate, isophorone diisocyanate (IPDI), 4,4'-dicyclohexylmethane diisocyanate (H$_{12}$MDI), cyclohexyl diisocyanate, 2,2,4-(2,2,4)-trimethylhexamethylene diisocyanate (TMDI), dimers prepared form aliphatic polyisocyanates, trimers prepared from aliphatic polyisocyanates and/or mixtures According to one or more of the embodiments described herein, the PTKUR formed with the hydroxyl terminated TK diol provides a bone cement, adhesive or filler that is hydrolytically stable and degradable by cell-secreted reactive oxygen species (ROS). For example, in some embodiments, the hydroxyl terminated TK diol provides a cross-linker that is selectively degraded by reactive oxygen species generated by cells during bone healing.

PTKUR and/or the prepared composites derived therefrom may include one or more additional components. In some embodiments, PTKUR and/or its composites may include, water, a catalyst (e.g., gelling catalyst, blowing catalyst, etc.), a stabilizer, a plasticizer, a porogen, a chain extender (for making of polyurethanes), a pore opener (such as calcium stearate, to control pore morphology) and a wetting or lubricating agent.

Additional Components

Other additional components include, but are not limited to, osteoconductivity enhancers. Suitable osteoconductivity enhancers may include ceramics, hydroxyapatite, pharmaceutically acceptable salts thereof, pharmaceutically acceptable derivatives thereof, or a combination thereof. For example, in one embodiment, 85% β-tricalcium phosphate (β-TCP)/15% hydroxyapatite (HA) ceramic mini-granules (MASTERGRAFT®, MG) is combined with hydroxyl terminated TK diols and polyisocyanate to form the PTKUR with increased osteoconductivity. In another embodiment, nanocrystalline hydroxyapatite is combined with hydroxyl terminated TK diol and polyisocyanate to form the PTKUR with increased osteoconductivity.

In some embodiments, at least one catalyst is added to form reactive liquid mixture of polyisocyanate and hydroxyl terminated TK diol. A catalyst, for example, can be nontoxic (in a concentration that may remain in the polymer).

A catalyst can, for example, be present in a concentration in the range of approximately 0.5 to 5 parts per hundred parts polyol (pphp) and, for example, in the range of approximately 0.5 to 2, or 2 to 3 pphp. A catalyst can, for example, be an amine compound. In some embodiments, the catalyst may be an organometallic compound or a tertiary amine compound. In some embodiments the catalyst may be stannous octoate (an organobismuth compound), triethylene diamine optionally in solution with dipropyleneglycol, bis(dimethylaminoethyl)ether, dimethylethanolamine, dibutyltin dilaurate, and Coscat organometallic catalysts manufactured by Vertullus (a bismuth based catalyst), or any combination thereof. In some embodiments, the catalyst includes iron (III) acetylacetonate (FeAA). For example, the catalyst may include a 5% solution of FeAA. In some embodiments, a nontoxic stabilizer can be added to PTKUR. Useful nontoxic stabilizers include a non-ionic surfactant, an anionic surfactant or combinations thereof. For example, a stabilizer can be a polyethersiloxane, a salt of a fatty sulfonic acid or a salt of a fatty acid. In certain embodiments, a stabilizer is a polyethersiloxane, and the concentration of polyethersiloxane in a reactive liquid mixture can, for example, be in the range of approximately 0.25 to 4 parts per hundred polyol. In some embodiments, polyethersiloxane stabilizer is hydrolyzable.

In some embodiments, plasticizers are based on an ester of a polycarboxylic acid with linear or branched aliphatic alcohols of moderate chain length. For example, some plasticizers are adipate-based. In some embodiments, polymers used as plasticizer are poly(ethylene glycol) (PEG). PEG used as a plasticizer is typically a low molecular weight PEG such as those having an average molecular weight of 1000 to 10000 g/mol, for example, from 4000 to 8000 g/mol.

In some aspects, porogens may be added to PTKUR prepared utilizing the hydroxyl terminate TK diols prepare according to processes described herein. Porogens can be any chemical compound that will reserve a space within the composite while the composite is being molded and will diffuse, dissolve, and/or degrade prior to or after implantation or injection leaving a pore in the composite.

A porogen may be a gas, liquid, or solid. Exemplary gases that may act as porogens include carbon dioxide, nitrogen, argon, or air. Exemplary liquids include water, organic solvents, or biological fluids (e.g., blood, lymph, plasma). Gaseous or liquid porogen may diffuse out of the osteoimplant before or after implantation thereby providing pores for biological in-growth. Solid porogens may be crystalline or amorphous. Examples of possible solid porogens include water soluble compounds. Exemplary porogens include carbohydrates (e.g., sorbitol, dextran (poly(dextrose)), starch), salts, sugar alcohols, natural polymers, synthetic polymers, and small molecules.

Preparation of Scaffold or Matrix

In one embodiment, forming a matrix or scaffold includes combining a poly(thioketal) polymer and a polyisocyanate, as discussed above, with a reactive liquid (i.e., a two-component composition) thereby forming a naturally injectable or moldable scaffold or a scaffold that can be made injectable or moldable. In another embodiment, forming scaffolds or matrices includes combining a hydroxyl-terminated TK with an excess of isocyanate to form a prepolymer, combining the prepolymer and additional hydroxyl-terminated TK, and then adding a catalyst to catalyze the reaction between the prepolymer and the hydroxyl-terminated TK. Suitable catalysts include, but are not limited to, a low-toxicity iron (III) acetylacetonate gelling catalyst. If present, the compounds, particles, and/or additional components, including any components to be delivered, may be combined with the polyisocyanate, hydroxyl-terminated TK, and/or PTK polymer at any point during the formation of the matrix, including, but not limited to, before, during, or after the combining of the polyisocyanate with the poly(thioketal) polymer and/or the hydroxyl-terminated TK.

In some embodiments, particles may be combined first with a hardener that can include a PTK polymer and, optionally, one or more of water, a catalyst, a solvent, a diluent, a stabilizer, a porogen, a plasticizer, and then the hardener is combined with a polyisocyanate. In some embodiments, a hardener (e.g., a PTK polymer, water and a catalyst) may be mixed with components to be delivered (e.g., biologically active agents) or components that are to be incorporated into the scaffold (e.g., porogens, bone powder, osteoconductivity enhancers).

In some aspects, PTK polymers may be first mixed with a solution of a catalyst and water, followed by addition of polyisocynates. The polyisocyanates described herein include various NCO-terminated compounds. In other embodiments, additional components or components to be delivered may be combined with a reactive liquid prior to injection. In some embodiments, they may be combined with one of intermediates (i.e., polyisocyanate, hydroxyl-terminated TK, and PTK polymers) prior to mixing the intermediates in forming of a reactive liquid/paste.

Polyurethanes (PUR) can be included with other material as part of composite materials, for example, with bone particles as described in U.S. Pat. No. 7,985,414, the contents of which are incorporated herein by reference. Such composite materials may be prepared by contacting an isocyanate-terminated prepolymer (e.g., a lysine ester triisocyanate-PEG prepolymer) with a polyol (e.g., a polyester polyol) or polyamine, and optionally with addition of water, a catalyst, a stabilizer, a porogen, PEG, an agent to be delivered to form the polyurethane.

In one embodiment, a polyurethane composite includes a polyurethane formed by reaction of a polyisocyanate such as, for example, lysine ester triisocyanate, with a hydroxyl-terminated TK diol (a polyol). In one embodiment, the composite includes an included material, for example, a biomolecule, extracellular matrix component, bioactive agent, small molecule, tissue-derived material, inorganic ceramic, bone substitute, a composite of an inorganic ceramic with one or more of a tissue-derived material, extracellular matrix material, or sugar (e.g., sucrose, dextrose) bovine serum albumin, or a mixture thereof.

The included material (e.g., bioactive agent, additional agent, bone material, and the like) in some embodiments, can be contacted with the polyol, in this application the hydroxyl-terminated TL diol, and then reacted with the polyisocyanate. The included material (e.g., bioactive agent, additional agent, bone material) in some embodiments, can be contacted with the polyisocyanate and then reacted with the polyol or polyamine. The included material (e.g., bioactive agent, additional agent, bone material, etc.) in some embodiments, can be contacted with both the polyol or polyamine and the polyisocyanate. In some embodiments, after the polyol or polyamine and the polyisocyanate are mixed, then the included material can be mixed with the prepolymer or the forming polyurethane.

In some embodiments, polyurethanes are often formed by the reaction of a polyisocyanate (such as a diisocyanate or a triisocyanate) with a polyol (such as a diol) as shown below:

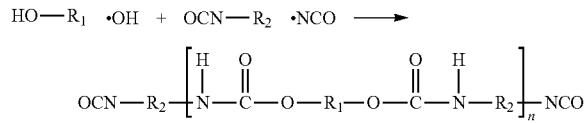

Polyurethanes may be straight chains or branched, and may have high or low molecular weights. Polyurethanes may also contain urea linkages formed by the reaction of an isocyanate with an amine. In an alternative embodiment, polyurethanes are formed by reacting a polyol such as the hydroxyl terminated TK diol with an excess of polyisocyanate to form a macropolyisocyanate prepolymer, following which the prepolymer is reacted with a second polyol to form the polyurethane as shown below:

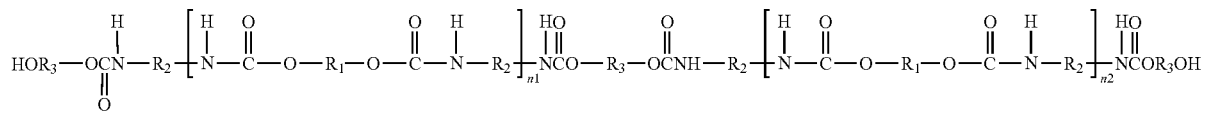

The $R_1$, $R_2$, and $R_3$ groups, which can be substituted and unsubstituted alkyl groups, cyclic and non-cyclic groups, provide great flexibility in tailoring the mechanical and chemical properties of polyurethanes, which may be made rigid, soft, plastic, and/or elastomeric by selection of appropriate functional groups, where n is the number of monomeric units in the polymer. The use of R groups having different types of chemical linkages creates regions of the polyurethane that are more and less flexible. For example, aromatic and polyaromatic R groups increase the rigidity of that segment of the polymer, while alkane and polyol chains are relatively flexible. The mixture of rigid, or hard, with flexible, or soft, segments in a polyurethane results in a strong, tough, elastomeric material. The ratio of hard and soft segments may be adjusted to optimize the mechanical properties of the composite.

Exemplary chain extenders that can be used in the polyurethane composition include, but are not limited to, 1,4-cyclohexane dimethanol, polyols of polyhydroxybutyrate or polyhydroxyvalerate, putrescine, polylactide, polyglycolide, poly(lactide-co-glycolide), biocompatible diester diols and diurea diols, 1,4-butanediol, ethylene diamine, 4,4'-methylene bis (2-chloroaniline), ethylene glycol, 3-hexyne-2,5-diol, 2-amino-1-butanol, or hexanediol or other aromatic and aliphatic diols or diamines.

In some embodiments, $R_1$, $R_2$, or $R_3$ of the formula above may include alkyl, aryl, heterocycles, cycloalkyl, aromatic heterocycles, multicycloalkyl, hydroxyl, ester, ether, carboxylic acid, amino, alkylamino, dialkylamino, trialkylamino, amido, alkoxy, or ureido groups.

Alternatively, or in addition, $R_1$, $R_2$, or $R_3$ may also include branches or substituents including alkyl, aryl, heterocycles, cycloalkyl, aromatic heterocycles, multicycloalkyl, hydroxyl, ester, ether, halide, carboxylic acid, amino, alkylamino, dialkylamino, trialkylamino, amido, carbamoyl, thioether, thiol, alkoxy, or ureido groups. Exemplary groups for use as $R_1$, $R_2$, or $R_3$ also include bioactive agents, biomolecules, and small molecules. Appropriate polyurethanes also include those disclosed in U.S. Patent Publication No. 2005/0013793, the contents of which are incorporated herein by reference.

In some embodiments, polyurethane composites are formed by reacting an appropriate polyisocyanate crosslinker (for example, a triisocyanate) or macropolyisocyanate prepolymer with a hydroxyl-terminated TK diol material to form composites which may have osteogenic and/or osteoinductive properties. In some embodiments, the material may have both amine and hydroxyl groups. The composites also may incorporate an included material, for example, a biomolecule, extracellular matrix component, bioactive agent, small molecule, bone, bone substitute, tissue derived material, inorganic ceramic, or a mixture of these. Details of traditional polyurethane synthesis can be found, for example, in Lamba, et al., *Polyurethanes in Biomedical Applications*, CRC Press, 1998, which is incorporated herein by reference, and particularly, in Chapter 2 of the above reference. The hydroxyl-terminated TK diol may serve as a polyol in a macropolyisocyanate, as a chain extender, or as any of $R_1$, $R_2$, or $R_3$.

Naturally derived materials may also be used as polyols or polyamines and may serve as part of the macropolyisocyanate, the chain extender, or both. In one embodiment, the hydroxyl-terminated TK diol is a biomolecule, for example, a lipid (e.g., phospholipid, lecithin, fatty acid, triglyceride, or cholesterol) or polysaccharide (e.g., oligosaccharide or amylase-resistant starches). A biomolecule for use according to the techniques of the present application may be hydroxylated by any method known to those skilled in the art if it does not already possess sufficient reactive groups to carry out a reaction. For example, lipids, including phospholipids, mono-, di-, and triglycerides, fatty acids, and cholesterols may require addition of hydroxyl or amine groups in order to carry out the polymerization reaction. In contrast, many polysaccharides already have sufficient hydroxyl groups to polymerize readily into a highly cross-linked polymer.

The hydroxylated material may also include intact extracellular matrix (ECM), its components, alone or in combination, or modified or synthetic versions thereof. These materials may be treated to increase the concentration of hydroxyl groups, especially the surface concentration of these groups. For example, collagen may be decross-linked or treated with lysyl oxidase. Lysyl oxidase converts the terminal amino groups of lysine to aldehydes, which may then be reduced. Alternatively or in addition, the biomolecule, or ECM component, or tissue may be aminated. The amino groups will be incorporated into the polymer through a urea linkage. Of course, many ECM derived materials already contain primary amino groups.

Exemplary extracellular matrix components suitable for use with the present application include, but are not limited to, collagen, laminin, elastin, proteoglycans, reticulin, fibronectin, vitronectin, glycosaminoglycans, and other basement membrane components. Various types of collagen (e.g., collagen Type I, collagen Type II, collagen Type IV, etc., as well as collagen derived or denatured materials such as gelatin) are suitable for use with the present application. Collagens may be used in fiber, gel, or other forms. Sources for extracellular matrix components include, but are not limited to, skin, tendon, intestine and dura mater obtained from animals, transgenic animals and humans. Collagenous tissue can also be obtained by genetically engineering microorganisms to express collagen as described, e.g., in U.S. Pat. No. 5,243,038, the entire contents of which are incorporated herein by reference. Procedures for obtaining and purifying collagen typically involve acid or enzyme extraction as described, e.g., in U.S. Pat. No. 5,263,984, the contents of which are incorporated herein by reference. The polyurethane matrix may include synthetic ECM analogs. Exemplary synthetic ECM analogs include RGD-containing peptides, silk-elastin polymers produced by Protein Polymer Technologies (San Diego, Calif.) and BioSteel™, a recombinant spider silk produced by Nexia Biotechnologies (Vaudrevil-Dorion, QC, Canada). Various types of collagen (e.g., collagen Type I, collagen Type II, collagen Type IV) are also suitable for use with embodiments of the present application.

The polyurethane matrix used with the present application may also include tissues including, but not limited to, xenograft, allograft, or autograft tissues, including non-bony tissues and bone-derived tissues. Non-bony tissues suitable for use with the application include connective tissue, such as tendon, ligament, cartilage, endodermis, small intestinal submucosa, skin, and muscle. The tissues may be excised and cut into a plurality of elongated fragments or particles employing methods known in the art. Reduction of the antigenicity of allogeneic and xenogeneic tissue can be achieved by treating the tissues with various chemical agents, e.g., extraction agents such as monoglycerides, diglycerides, triglycerides, dimethyl formamide, etc., as described, e.g., in U.S. Pat. No. 5,507,810, the contents of which are incorporated herein by reference. Small intestine submucosa tissue can be obtained and processed as described in U.S. Pat. No. 4,902,508, the contents of which are incorporated herein by reference. In summary, intestinal tissue is abraded to remove the outer layers, including both the tunica serosa and the tunica muscularis and the inner layers, including at least the luminal portion of the tunica mucosa. The resulting material is a whitish, translucent tube of tissue approximately 0.1 mm thick, typically consisting of the tunica submucosa with the attached lamina muscularis mucosa and stratum compactum. The tissue may be rinsed in 10% neomycin sulfate before use. Tissues may be modified by demineralization, amination, or hydroxylation before use. For example, lysine groups may be modified with lysyl oxidase as described above.

Ceramics may also be included in the polyurethane before, during or after it is made. Ceramics, including calcium phosphate materials and bone substitute materials, may also be exploited for use as particulate inclusions or as the hydroxyl-terminated TK diol that can be in the polyurethane matrix. Exemplary inorganic ceramics for use with the present application include calcium carbonate, calcium sulfate, calcium phosphosilicate, sodium phosphate, calcium aluminate, calcium phosphate, hydroxyapatite, alpha and/or beta tricalcium phosphate, dicalcium phosphate, tetracalcium phosphate, amorphous calcium phosphate, octacalcium phosphate, or BIOGLASS™, a calcium phosphate silica glass available from U.S. Biomaterials Corporation. Substituted CaP phases are also contemplated for use with the present application including, but not limited to, fluorapatite, chlorapatite, Mg-substituted tricalcium phosphate, and carbonate hydroxyapatite. Additional calcium phosphate phases suitable for use with the present application include those disclosed in U.S. Pat. Nos. RE 33,161 and RE 33,221 to Brown et al.; U.S. Pat. Nos. 4,880,610; 5,034,059; 5,047,031; 5,053,212; 5,129,905; 5,336,264; and U.S. Pat. No. 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al.; U.S. Pat. Nos. 5,717,006 and 6,001,394 to Daculsi et al.; U.S. Pat. No. 5,605,713 to Boltong et al.; U.S. Pat. No. 5,650,176 to Lee et al.; and U.S. Pat. No. 6,206,957 to Driessens et al.; and biologically-derived or biomimetic materials such as those identified in Lowenstam, H. A. and Weiner S., *On Biomineralization*, Oxford University Press, 1989, all of which are incorporated herein by reference. The composite may contain between about 5% and 80% bone-derived or other ceramic material, for example, between about 20% to about 60%, or between about 30% to about 50% bone-derived or other ceramic material.

In some embodiments, a composite material may be reacted with a macropolyisocyanate to form a polyurethane composite. For example, inorganic ceramics such as those described above or bone-derived materials may be combined with proteins such as BSA, collagen, or other extracellular matrix components such as those described above to form a composite. Alternatively, or in addition, inorganic ceramics or bone-derived materials may be combined with synthetic or naturally-derived polymers to form a composite using the techniques described in our co-pending applications U.S. Ser. No. 10/735,135 filed Dec. 12, 2003; U.S. Ser. No. 10/681,651 filed Oct. 8, 2003; and U.S. Ser. No. 10/639,912 filed Aug. 12, 2003, the contents of all of which are incorporated herein by reference. These composites may be lightly demineralized as described below to expose the organic material at the surface of the composite before they are formed into polyurethane composites according to the teachings of the present application.

When the hydroxyl-terminated TK diol is difunctional, reaction with a triisocyanate generally produces a polyurethane with minimal crosslinking. Such polymers are generally thermoplastic and readily deformable and may be subjected to strain-induced crystallization for hardening. In contrast, if at least some reactants include at least three active groups participating in the reaction, then the polymer will generally be heavily cross-linked. Such polymers are often thermosets and tend to be harder than polymers with low cross-linking. In addition, their mechanical properties tend to be less dependent on how they are processed, which may render them more machinable. Cross-linking may also be controlled through the choice of catalyst. Exemplary catalysts include mild bases, strong bases, sodium hydroxide, sodium acetate, tin, and triethylene diamine-1,4-diaza (2,2,2)bicyclooctane. The stoichiometry and temperature of the reaction may also be adjusted to control the extent of crosslinking.

Because the reaction process combines an isocyanate with a biomolecule or other biological or biocompatible material, many possible breakdown products of the polymer according to certain embodiments are themselves resorbable. In one embodiment, byproducts of enzymatic degradation, dissolution, bioerosion, or other degradative processes are biocompatible. These byproducts may be utilized in or may be metabolites of any cellular metabolic pathway, such as but not limited to cellular respiration, glycolysis, fermentation, or the tricarboxylic acid cycle. In one embodiment, the polyurethanes of the present application are themselves enzymatically degradable, bioerodable, hydrolyzable, and/or bioabsorbable. Thus, when an osteoimplant is formed from the materials of the present application, it can be slowly replaced by the ingrowth of natural bone as the implant degrades. This process of osteogenesis may be accelerated, for example, by the addition of bioactive agents. Such bioactive agents may be incorporated into the polymer structure, either as backbone elements or as side groups, or they may be present as solutes in the solid polymer or as non-covalently bonded attachments or they may be part of the polyurethane when it is formed. In any case, they may be gradually released as the polyurethane degrades. The rate of release may be tailored by modifying the attachment or incorporation of the bioactive agents into the polymer. Bioactive agents that may be used include not only agents having osteogenic properties, but also agents having other biological properties such as immunosuppression, chemoattraction, antimicrobial properties, etc.

Exemplary bioactive agents include bone stimulating peptides such as RGD, bone morphogenic proteins, and other growth factors, antibiotics, etc. Lectins are a class of particular interest for incorporation into the present polymers, especially when the polymers comprise carbohydrates, which bond readily to lectins.

In some embodiments, the biodegradable matrix can comprise sugar (e.g., dextrose, sucrose, etc.) and/or bone particles or bone substitute materials as described in U.S. Pat. No. 7,985,414. The entire disclosure of this reference is herein incorporated by reference into the present disclosure.

For certain applications, it may be desirable to create foamed polyurethane, rather than solid polyurethane. While typical foaming agents such as hydrochlorofluorocarbons, hydrofluorocarbons, or pentanes may not be biocompatible for many systems, other biocompatible agents may be used. For example, water, and ascorbic acid may be an adequate foaming agent for a lysine triisocyanate/PEG/glycerol polyurethane. Other foaming agents include dry ice or other agents that release carbon dioxide or other gases into the composite. Alternatively, or in addition, salts may be mixed in with the reagents and then dissolved after polymerization to leave behind small voids.

Whether foamed or solid, polyurethanes may be formed with an additional, included material. Exemplary included materials include, but are not limited to, bone-derived tissue, non-bone derived tissue, and ceramics and bone substitute materials. In some embodiments, settable osteogenic materials (e.g. alpha-BSM, available from ETEX Corp., Cambridge, Mass., Norian SRS, (Skeletal Repair System) available from Norian Corp., Cupertino, Calif., or Dynaflex, available from Citagenix) are included in the polyurethane composite. These materials may bond strongly to the polyisocyanates used in forming the polymer, since they contain or may be modified to contain significant numbers of active hydroxyl groups. Thus, it may be preferred in some embodiments to first mix the included material with the hydroxyl-terminated TK diol, before addition of the polyisocyanate. Nevertheless, it is also within the scope of the present application to mix the additional material into already-combined hydroxyl-terminated TK diol and polyisocyanate, or to combine all three components simultaneously. The amount of included material in the composite will vary depending on the desired application, and practically any amount of material, for example, at least 10%, at least 30%, at least 50%, or at least 70% of the composite may be formed from the included material.

In some embodiments, the polyurethane matrix comprises a plurality of pores to allow ingrowth of tissue (e.g., bone tissue) to repair bone. In some embodiments, at least 10% of the pores are between about 10 micrometers and about 500 micrometers at their widest points. In some embodiments, at least 20% of the pores are between about 50 micrometers and about 150 micrometers at their widest points. In some embodiments, at least 30% of the pores are between about 30 micrometers and about 70 micrometers at their widest points. In some embodiments, at least 50% of the pores are between about 10 micrometers and about 500 micrometers at their widest points. In some embodiments, at least 90% of the pores are between about 50 micrometers and about 150 micrometers at their widest points. In some embodiments, at least 95% of the pores are between about 100 micrometers and about 250 micrometers at their widest points. In some embodiments, 100% of the pores are between about 10 micrometers and about 300 micrometers at their widest points.

In some embodiments, the biodegradable polyurethane or polyurea matrix comprises pore sizes from about 0.01 microns to about 1 mm or from about 0.02 microns to about 2 mm.

In some embodiments, the polyurethane matrix of the present application comprises a wet compressive strength of at least about 1 MPa to about 150 MPa, at least about 3 MPa to about 100 MPa, at least about 5 MPa to about 80 MPa, at least about 10 MPa to about 70 MPa at least about 20 MPa to about 60 MPa, or at least about 30 MPa to about 50 MPa.

These and other aspects of the present application will be further appreciated upon consideration of the following Examples, which are intended to illustrate certain particular embodiments of the application but are not intended to limit its scope, as defined by the claims.

EXAMPLES

In these examples, all chemicals were purchased from Sigma-Aldrich (Milwaukee, Wis., USA) or where otherwise commercially available.

Example 1—Preparation of Thioketal Diol Via Thioketal Diacid Intermediate

This example describes the synthesis of a thioketal (TK) diol monomer prepared based on a thioketal diacid intermediate. In a 5 L jacketed vessel, 6 g (0.017 equivalents) of bismuth chloride was dissolved in 3 L of acetonitrile. Once the solution was dissolved, 200 g of 2,2-dimethoxypropane and 354 g (1 equivalent) of thioglycolic acid are added to the reaction mixture. The solution was then diluted with 500 mL with acetonitrile (ACN), placed under a nitrogen blanket and heated to 45° C. for 24 hours. After 24 hours, the solvent was removed by rototary evaporation to yield a white powder with some remaining starting material. The solid residue was then washed twice with 500 mL dichloromethane (DCM) before drying under vacuum to yield a powder (typically 100 g of a white-yellow crystalline material).

The dried powder was then dissolved in 5 volumes of anhydrous tetrahydrofuran (THF) and placed into an addition funnel. In a 5 L jacketed reactor, 1 L of 1M LiAlH$_4$ in THF was added under nitrogen and cooled to −40° C. The TK diol solution was added to the reactor slowly, making sure the temperature of the vessel did not increase above 0° C. during the addition. After adding all the TK diol solution, the solution was mixed at this temperature for 30 minutes before slowly allowing it to come to room temperature while stirring it for 24 hours.

The reaction mixture was cooled to −20° C. and quenched with 1 L of THF/H2O (50/50 v:v), making sure the temperature never increased above 5° C. After stirring for 30 minutes, 500 mL (2.5 equivalents) of isopropyl alcohol (IPA) and acetonitrile were added to the mixture and stirred for 30 additional minutes. The solution was then filtered and the solvent removed by rotary evaporation (40° C.). The resulting concentrate was then washed with 400 mL of 1M sodium citrate (pH 7) and 500 mL of DCM. The aqueous fraction was washed three more times with 500 mL of DCM. The combined organic phases were dried over MgSO$_4$, filtered and concentrated to give 30 g of final product.

Example 2—Preparation of Thioketal Diol Via Thioketal Diacid Intermediate Comparative Example In another typical synthesis of thioketal diol wherein a thioketal diacid intermediate is formed, bismuth (III) chloride was added to a dry boiling flask that was subsequently dried with a hot air gun under vacuum for about 5 minutes to ensure completely dry catalyst conditions. The flask was then purged with nitrogen and left under a positive pressure with nitrogen for the remainder of the reaction. Anhydrous acetonitrile was charged to the flask to dissolve the catalyst. 2,2-dimethoxypropane and thioglycolic acid were added to the flask, and the reaction was allowed to proceed for 24 hours while stirring at room temperature.

Following the reaction, the carboxyl-terminated intermediate was filtered with a Buchner funnel, rotary evaporated (Buchi Rotary evaporation R-200, 35° C.), and dried under vacuum overnight. The carboxyl groups were then reduced to produce a hydroxyl-terminated TK. To reduce the carboxyl groups and produce the hydroxyl-terminated TK, a 3-neck boiling flask was fitted to a 10° C. condenser capped with a 1-way glass stop-cock, a constant pressure dropping funnel, and a rubber stopper. The reactor was heated with a heat gun under vacuum for about 5 minutes to ensure completely dry reaction conditions. The reactor was then placed in an ice bath, purged with dry nitrogen, and maintained under positive pressure with nitrogen throughout the functionalization. Lithium aluminum hydride (LiAlH$_4$) was added to the 3-neck boiling flask and dissolved in diethyl ether. Using anhydrous techniques, anhydrous tetrahydrofuran was added to the boiling flask containing the carboxyl-terminated TK. The resulting solution was then transferred to the dropping funnel and added to the LiAlH$_4$ solution dropwise at 0° C. After all the TK solution was added, the ice bath was replaced with an oil bath and the reaction mixture was refluxed at 52° C. for 6-8 hours. Unreacted LiAlH$_4$ was quenched by adding deionized water dropwise followed by 1M sodium hydroxide to aid in product extraction. By-products of the reaction were filtered using a Buchner funnel and filtration flask, and a separation funnel and diethyl ether were used to extract and isolate the TK diol product. The solvent was removed by rotary evaporation and the product dried under vacuum overnight for a completely dry, solvent-free TK diol.

Example 3—Preparation of Thioketal Diol Via Thioketal Diester Intermediate

This example describes the synthesis of a thioketal (TK) diol monomer prepared based on a thioketal diester intermediate. In a 5 L jacketed vessel, 6 g of bismuth chloride was dissolved in 3 L of acetonitrile (ACN). Once the solution was dissolved, 200 g of 2,2-dimethoxypropane and 407 g of methyl thioglycolate were added to the reaction mixture. The solution was then diluted with 500 mL with acetonitrile, placed under a nitrogen blanket and heated to 50° C. for 72 hours. After 72 hours, the solvent was removed by rotary evaporation to yield a red liquid with quantitative yield. The liquid was confirmed by NMR for structure.

The product (200 g) from the previous step was then dissolved in 5 volumes of methyl THF and placed into an addition funnel. In a 5 L jacketed reactor, 534 g of Red-Al (sodium bis(2-methoxyethoxy) aluminum hydride) in toluene was added under nitrogen and diluted with 1 L of anhydrous toluene before cooling to −40° C. The TK ester solution was added to the reactor slowly, making sure the temperature of the vessel does not increase above 0° C. during the addition. After adding all the diester solution, the solution was mixed at temperature for 30 minutes before slowly allowing it to come to room temperature and stirred for 24 hours.

The reaction mixture is cooled to −20° C. and quenched with 1 L of MeTHF/IPA (50/50 v:v), making sure the temperature never increased above 5° C. After final addition, the reaction was stirred for 30 minutes before adding 500 mL 1N KOH in MeOH/water (50:50 v:v) to the mixture very slowly making sure the temperature of the vessel did not increase above 0° C. during the addition. After all the potassium hydroxide was added and the exotherm was complete, the reaction was stirred for 30 additional minutes before warming to room temperature. The mixture formed two phases. The supernate was filtered through a ½" celite bed to give a clear yellow solution that rapidly turned orange in air. The solution was concentrated on a rotovap (45° C.). The resulting concentrate was then dissolved in 500 mL of ethyl acetate and washed with 500 mL of 50% brine, sodium bicarb, and brine. The aqueous fractions were combined and backwashed twice with 500 mL of ethyl acetate. The organic phases were combined and dried over Na$_2$SO$_4$. The solution was filtered and concentrated on a rotovap (45° C.). The concentrated intermediate was then purified on a Snap Ultra (350 g) with no more than a 15% weight load on an 7% MeOH in DCM isocratic elution. All products eluted after 2.4 column volumes (CV). Like fractions were combined and concentrated on a rotovap (50° C.) to give about 40 g of final product.

Example 4—Procedure for Purification of Thioketal Diol

Figure 4:
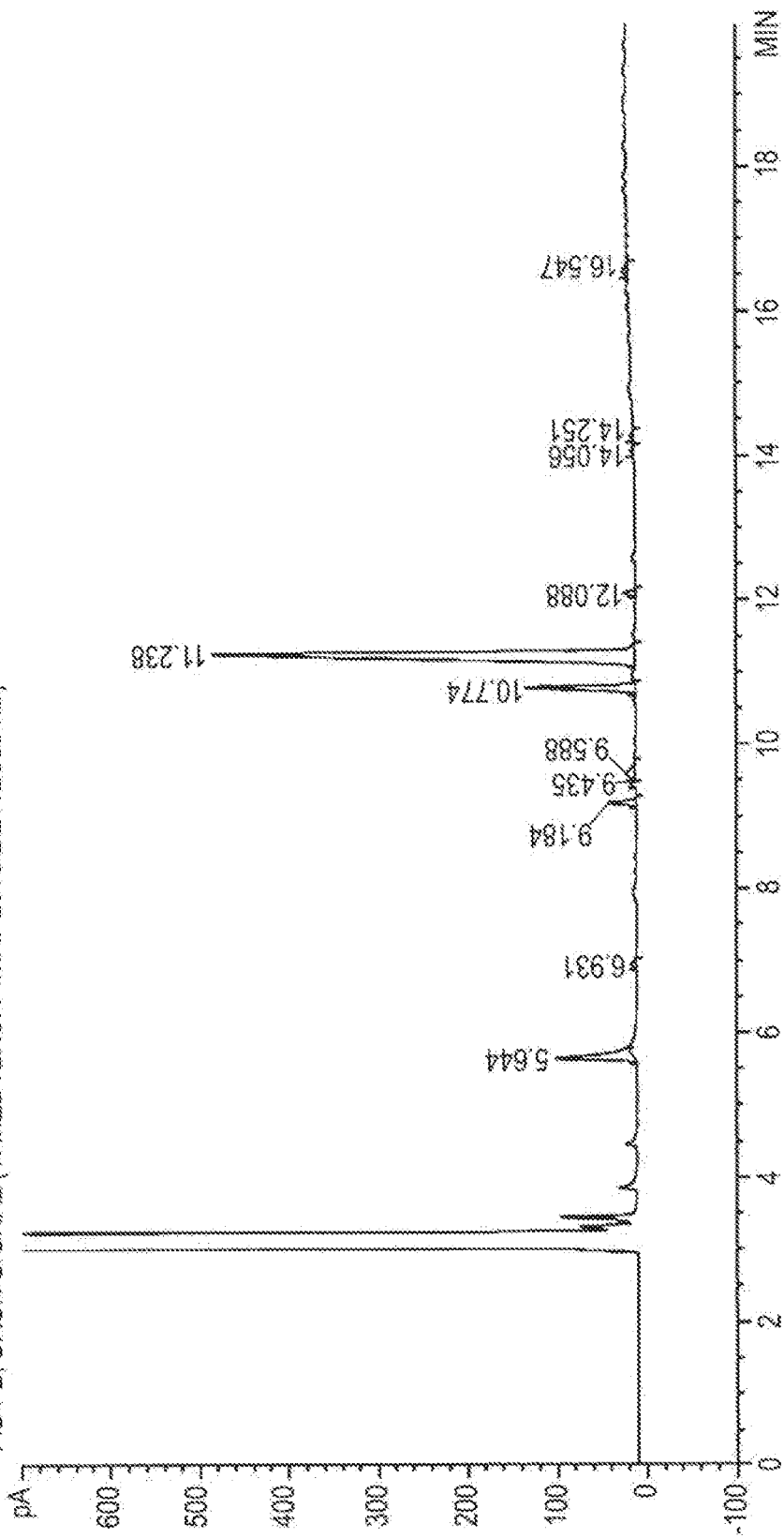
FIG. 4 is a graphic illustration of GC-FID data obtained for tioketal diol prepared by a diester intermediate process before column purification yielding 71.0% purity (batch RD041)
Figure 5:
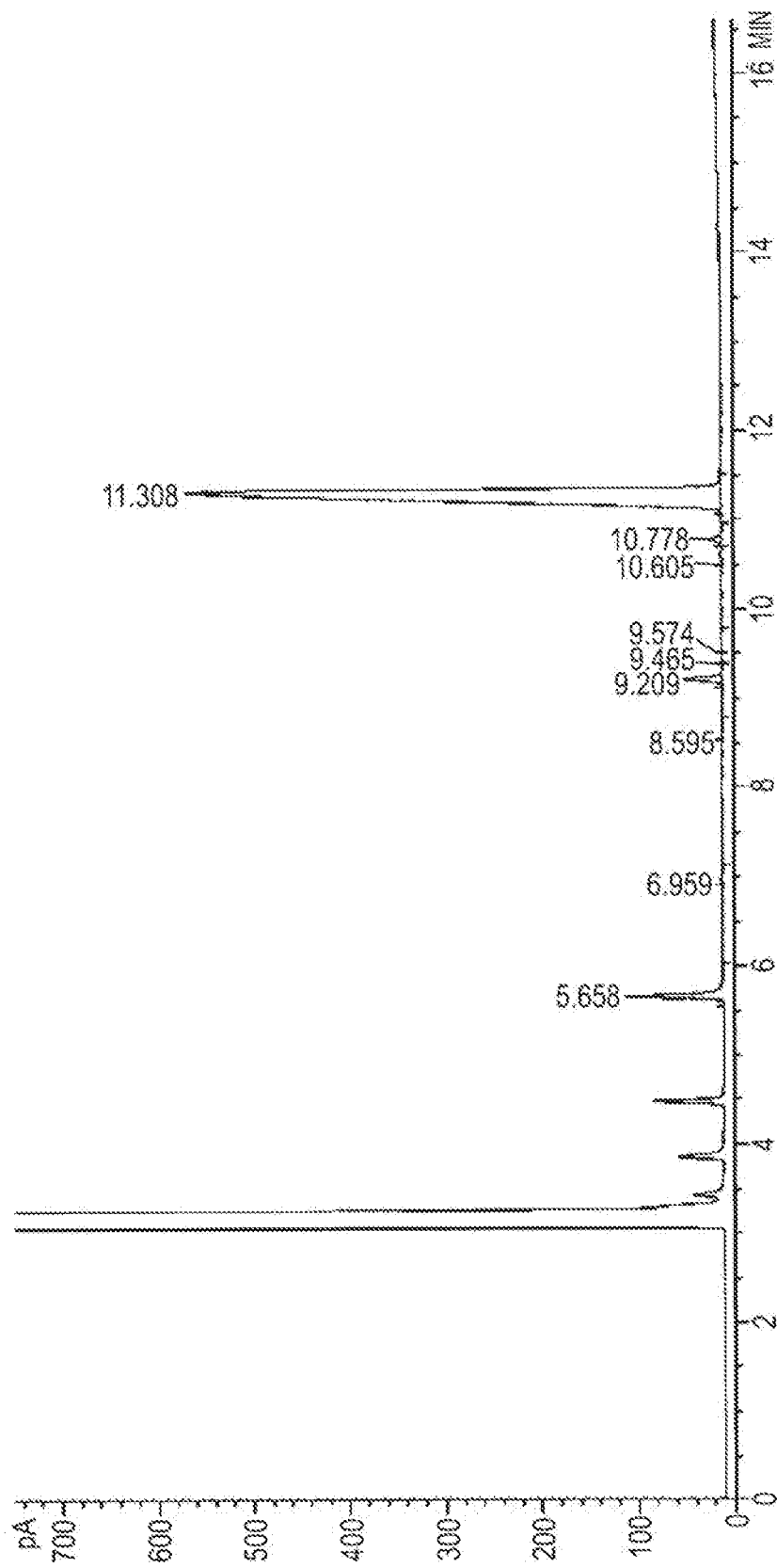
FIG. 5 is a graphic illustration of the GC-FID data obtained for thioketal diol prepared by a thioketal diester intermediate process after column purification yielding 90.0% purity (batch RD041)

This example describes a procedure used for purifying thioketal diol synthesized by preparing a thioketal diester intermediate. First, the amount in grams of thioketal (TK) diol for purification was determined. A column of silica gel was prepared where the amount of silica gel was seven-fold the amount of TK diol to be purified. The silica gel was suspended in dichloromethane (DCM) and then loaded onto a column, tapping the column to eliminate air bubbles. TK diol dissolved in DCM was loaded onto the column in even coating to maximize separation from impurities. The column bed was covered with sand to prevent disturbing the bed during solvent loading. A 6% MeOH/DCM mixture was prepared to be used as the mobile phase to be added to the silica and the column as eluent. Various fractions representing compounds present in the crude TK diol could have different colors, some of which could be bright. The TK diol product was present in a deep amber colored fraction. After NMR confirmation, the product presence was confirmed by TLC having the same mobile phase as the column. A typical mass recovery was 95%. FIGS. 4 and 5 illustrate GC-FID graphs for TK diol (batch RD041) prepared by a diester intermediate process before column purification having a 71.0% purity and after column purification yielding a 90.0% purity.

Example 5—Carbon Treatment Procedure for TK Diol

In this procedure, crude TK diol prepared by reduction with RedAl was treated with decolorizing carbon in order to improve the visual quality of the product. 5 g of crude TK diol mixture was dissolved in 20 mL of DCM. 0.5 g of ground Norit decolorizing carbon was added to the dissolved TK diol mixture. The mixture was filtered to remove solids. The solution was then concentrated and purified by biotage column chromatography. The collected fractions were tested by TLC and the majority fractions were combined and concentrated. The final material was tested for color structure by IR/NMR.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of making a hydroxyl-terminated thioketal diol, the method comprising reacting a thioketal ester with a non-pyrophoric reducing agent to form a hydroxyl-terminated thioketal diol, wherein the thioketal ester is dimethyl 2,2-(propane-2,2-diylbis(sulfanediyl)) diacetate.

2. The method of claim 1, wherein the hydroxyl-terminated thioketal diol is 2,2-(propane-2,2-diylbis(sulfanediyl)) diethanol.

3. The method of claim 1, wherein the non-pyrophoric reducing agent comprises (i) sodium aluminum hydride, or (ii) sodium bis (2-methoxyethoxy)aluminum hydride.

4. The method of claim 1, wherein the thioketal ester is prepared by reacting a thioglycolic acetate with a methoxy functional compound in the presence of bismuth (III) chloride.

5. The method of claim 4, wherein the thioglycolic acetate is methyl 2-mercaptoacetate.

6. The method of claim 4, wherein the methoxy functional compound is 2,2-dimethoxypropane.

7. A method of making a hydroxyl terminated thioketal of formula I

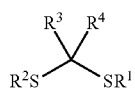

wherein $R^1$ and $R^2$ are $CH_2CH_2OH$; and
$R^3$ and $R^4$ are independently $CH_3$, $CH_2CH_3$, $(CH_2)_2CH_3$ or $(CH_2)_3CH_3$, the method comprising:
(i) reacting a thioglycolic acetate with a methoxy functional compound in the presence of bismuth (III) chloride to obtain a thioketal ester having formula I except where $R^1$ and $R^2$ are both $CH_2C(O)OCH_3$; and (ii) reacting the thioketal ester with a non-pyrophoric reducing agent to form a hydroxyl-terminated thioketal diol where $R^1$ and $R^2$ are both $CH_2CH_2OH$.

8. The method of claim 7, wherein (i) the thioglycolic acetate is methyl 2-mercaptoacetate, the methoxy functional compound is 2,2-dimethoxypropane; (ii) the reducing agent is a sodium aluminum hydride and (iii) the thioketal ester is dimethyl 2,2-(propane-2,2-diylbis(sulfanediyl)) diacetate.

9. The method of claim 8, wherein the hydroxyl-terminated thioketal diol is reacted with an isocyanate to form a biodegradable matrix.

10. The method of claim 9, further comprising mixing the biodegradable matrix with a reinforcement material, the reinforcement material comprising (i) a bone or bone substitutes; or (ii) calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms thereof.

11. The method of claim 9, wherein the isocyanate is lysine diisocyanate, lysine triisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates.

12. The method of claim 9, further comprising mixing the biodegradable matrix with a bioactive agent.

13. A method of making a biodegradable polyurethane composite, the method comprising (i) reacting a thioketal diester with a non-pyrophoric reducing agent to form a hydroxyl-terminated thioketal diol, (ii) reacting the hydroxyl-terminated thioketal diol with an isocyanate and a reinforcement material to form the biodegradable polyurethane composite, wherein the thioketal diester is dimethyl 2,2-(propane-2,2-diylbis(sulfanediyl)) diacetate.

14. The method of claim 13, wherein the reacting in step (ii) comprises mixing the hydroxyl-terminated thioketal diol with the isocyanate to form a mixture; and mixing the mixture with the reinforcement material to form the biodegradable polyurethane composite.

15. The method of claim 14, wherein the mixture comprises crosslinked polyurethane.

16. The method of claim 13, wherein the reacting in step (ii) comprises exposing the thioketal diol, a polyisocyanate and the reinforcement material to a catalyst.

17. The method of claim 16, wherein the catalyst comprises (i) an amine or an organometallic compound; (ii) triethylene diamine, bis(dimethylaminoethyl)ether or dimethylethanolamine; (iii) stannous octoate or dibutyltin laurate; or (iv) iron (III) acetyl acetatonate.

18. The method of claim 13, wherein the reinforcement material comprises calcium carbonate, calcium sulfate, calcium phosphosilicate, sodium phosphate, calcium aluminate, calcium phosphate, calcium carbonate, hydroxyapatite, demineralized bone, mineralized bone, or combinations thereof.

19. The method of claim 13, further comprising adding a bioactive agent to the polyurethane composite.

20. The method of claim 13 wherein the thioketal diester is prepared by reacting a thioglycolic acetate with a methoxy functional compound in the presence of bismuth (III) chloride.

* * * * *